United States Patent [19]

Gruss et al.

[11] Patent Number: 6,025,190
[45] Date of Patent: Feb. 15, 2000

[54] TEMPERATURE-SENSITIVE PLASMID

[75] Inventors: Alexandra Gruss, Paris; Emmanuelle Maguin, Montrouge, both of France

[73] Assignee: Institut National de la Recherche Agronomique, Paris, France

[21] Appl. No.: 08/302,752
[22] PCT Filed: Mar. 12, 1993
[86] PCT No.: PCT/FR93/00248
  § 371 Date: Dec. 27, 1994
  § 102(e) Date: Dec. 27, 1994
[87] PCT Pub. No.: WO93/18164
  PCT Pub. Date: Sep. 16, 1993

[30] Foreign Application Priority Data

Mar. 13, 1992 [FR] France ................................ 92 03034

[51] Int. Cl.⁷ ........................... C12N 15/63; C12N 15/70; C12N 15/74; C12N 1/21
[52] U.S. Cl. .................. 435/320.1; 435/69.1; 435/172.3; 435/252.3; 435/252.31; 435/252.33
[58] Field of Search .............................. 435/320.1, 172.3, 435/252.3, 252.31, 252.33, 69.1, 71.1; 536/23.1, 24.1; 935/22, 33, 38, 43, 66, 72, 73, 74

[56] References Cited

U.S. PATENT DOCUMENTS 4,711,845  12/1987  Gelfand et al. ......................... 435/69.1

FOREIGN PATENT DOCUMENTS

| 0182562 | 5/1986 | European Pat. Off. . |
| 0243856 | 11/1987 | European Pat. Off. . |
| 0334282 | 9/1989 | European Pat. Off. . |
| 0445385 | 9/1991 | European Pat. Off. . |

OTHER PUBLICATIONS

Applied and Enviromental Microbiology; vol. 57, No. 2, 1991, Washington DC, pp. 539–548. Feiertag J M; Petzel J P; Pasalodos E; Baldwin K A; McKay L L "Thermosensitive Plasmid Replication Temperature–Sensitive Host Growth and Chromosomal Plasmid Integration Conferree by Lactococcus–Lactis–SSP–Cremoris Lactose Plasmids in Lactococcus–Lactis–SSP–Lactis" see the whole document. Relevant to Claims 1–4, 19–24.

Journal of Bacteriology; vol. 172, No. 8, 1990, Baltimore, U.S., pp. 4543–4584. Sozhammannan S; Dabert P; Moretto V; Ehrlich S D; Gruss A "Plus–Origin Mapping of Single–Stranded DNA Plasmid P–E–194 and Nick Site Homologies With Other Plasmids" cited in the application. See the whole document. Relevant to Claims 1,2,19–24.

Biological Abstracts; vol. 87 Philadelphia, PA, U.S., abstracts No. 047423. Alonso J C; Stiege C A; Tailor R H; Viret J–F "Functional Analysis of the DNA–TS Mutants of Bacillus–Subtilis Plasmid PUB110 Replication As A Model System"; see abstract & Mol Gen Genet 214 (3). 1988. 482–489. Relevant to Claims 1,9–11.

Biological Abstracts; vol. 92, Philadelphia, PA, U.S., abstract No. 075453. Leenhouts K J; Kok J; Venema G "Replacement Recombination In Lactococcus–Lactis"; see abstract & J. Bacteriol 173 (15). 1991. 4794–4798. Relevant to Claims 5, 8.

Biological Abstracts; vol. 88, Philadelphia, PA, U.S., abstract No. 107483. Priebe S D; Lacks S A "Region Of The Streptococcal Plasmid PMV158 Required For Conjugative Mobilization"; see abstract & J. Bacteriol 171 (9). 1989. 4778–4784. Relevant to Claim 15.

Journal of Bacteriology; vol. 174, No. 17, 1992, Baltimore U.S., pp. 5633–5638. Maguin E; Duwat P; Hege T; Ehrlich D; Gruss A "New Thermosensitive Plasmid For A Gram–Positive Bacteria"; see the whole document. Relevant to Claims 1–24.

Alonso et al. "Functional Analysis of the dna (Ts) Mutants of *Bacillus subtilis*" Mol Gen Genet 214 482–489 1988.

Danilevich et al. "Isolatin & Characterization of a Temperature–Sensitive Plasmid . . . " Mol Biol 18(4) 1111–1120 1984. Abstract only.

Urlapova et al. "Temperature Sensitive Mutants of the Plasmid RP–1" Genetika 15(3) 1979 433–443. Abstract only.

Leenhouts et al. "Nucleotide Sequence & Charcterization of the Broad Host Range Lactococcal Plasmid pWVO1" Plasmid 26 55–66 1991.

*Primary Examiner*—Nancy Degen
*Attorney, Agent, or Firm*—Christie, Parker & Hale, LLP

[57] ABSTRACT

A bacterial vector plasmid of the type having an efficient replication origin in Gram-positive bacteria. The plasmid is characterized by having at least one marker gene which expresses itself in a bacterial host strain, an efficient replication system which is thermosensitive based on a temperature compatible with the viability of the host strain, and in that the temperature of replication inhibition is below or equal to approximately 37° C. The invention also concerns bacteria containing the plasmid and a process for inactivating a gene in the chromosome of a bacterium.

19 Claims, 21 Drawing Sheets

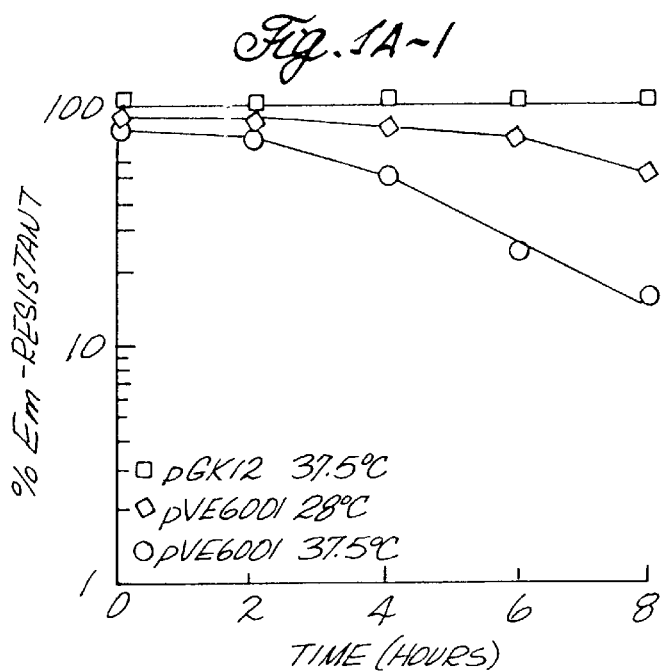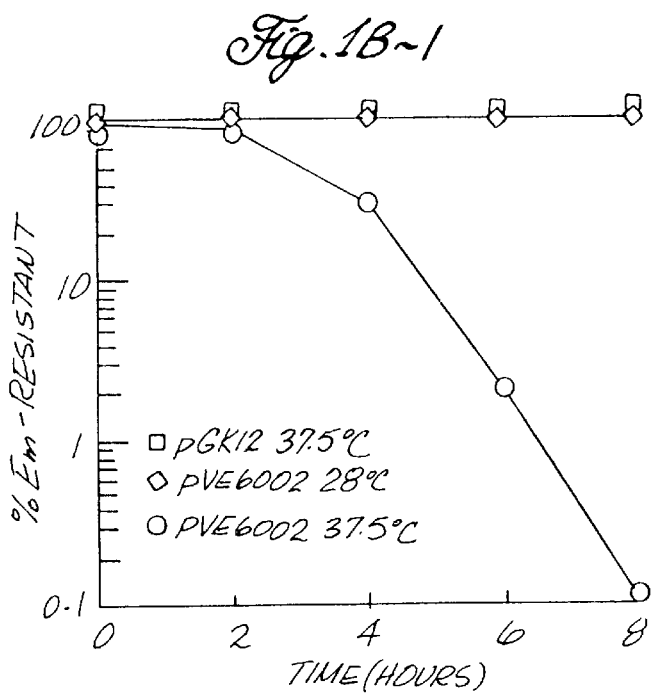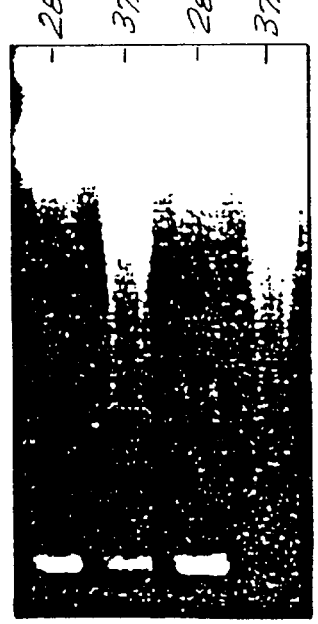

Fig. 5

```
               50              60              70            80
PE.194    LHDRDTDTEGRM..........................KKEHYHILVMYEGNKSYEQI
          ***  *                                ** ***  * ***** ***
PLB.4     LHDKDVNPDGEK..........................KKSHYHLVLNYKGNKSEEQI
          ***** *   *                           ** *  *  * ***  * *
PHPK.255  LHDKDLNEDGSH..........................KKPHFHAIIVFDKKQRPAAV
          ***** *                               ****  *              *
PADB.201  LHDKDVNPDGTI..........................KKPHYHIVLAYSGPTTFNNV
          *****                                 ** ***    *       *
PLS.1     LHDKDKSSIKGQKY.........................KKAHYHVLYIAKNPVTADSV
          ****  *                               ** ***** *  *  *  **
PWV.01    LHDMDEKLDKDTWNSSDVIRNGKH.YKKPHYHVIYLARNPVTIESV
          ******* ************** * ***** ****************
PHS.71    LHDMDEKKDKDTWNSSDVIRNGKH.YKKPHYHVIYIARNPVTIESV
          ********* *              *  *  **********
PFX.2     LHDMDEKKIKIHGIVVMLYEMEMHVIKNPHYHVILHGNPVTIESV
                                                    **************

CONSENS   LHD D                                 KKPHYH      P T E V
               50       60          70     80
               70       80         90      100
```

Integration of the Ts plasmid in the chromosome

The gene is inactivated by the integrated plasmid

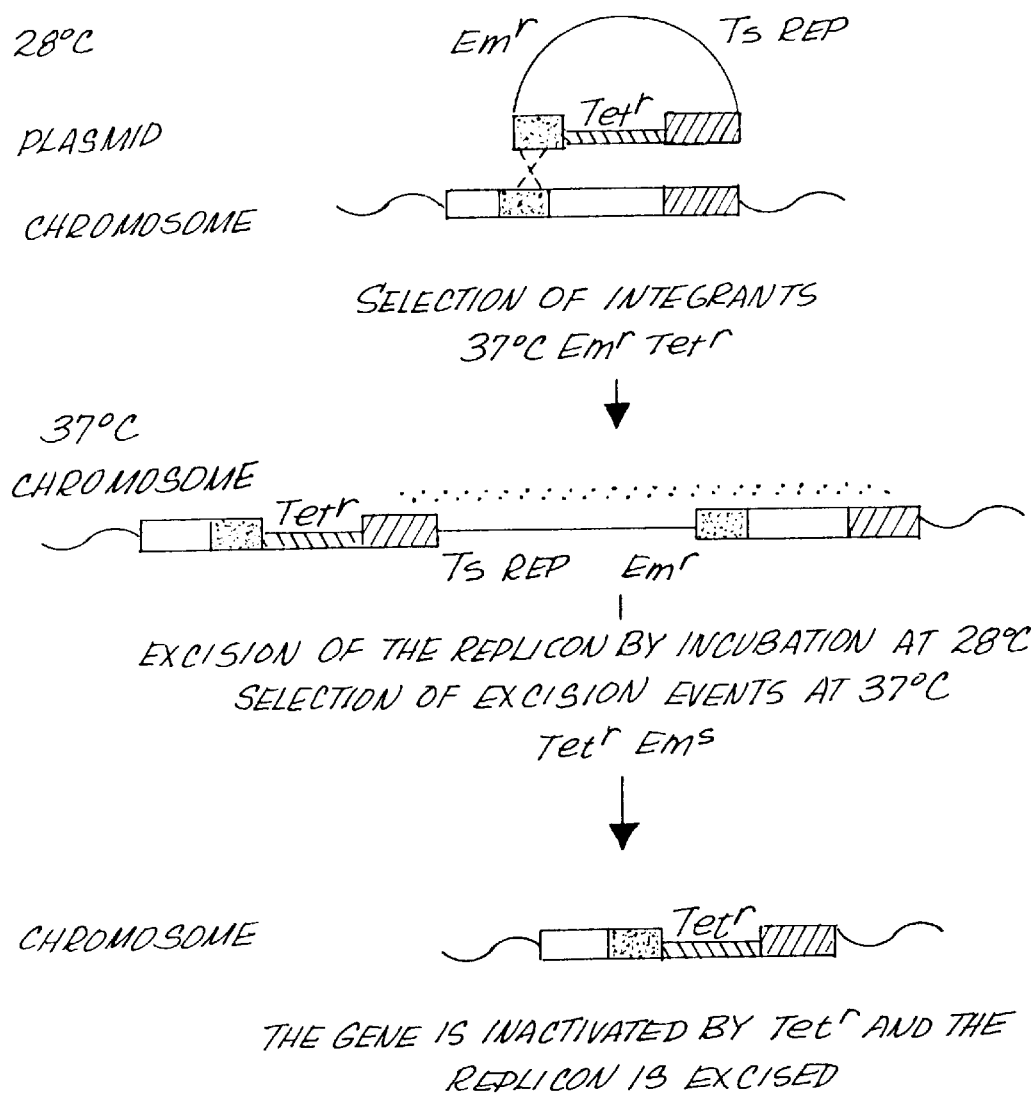

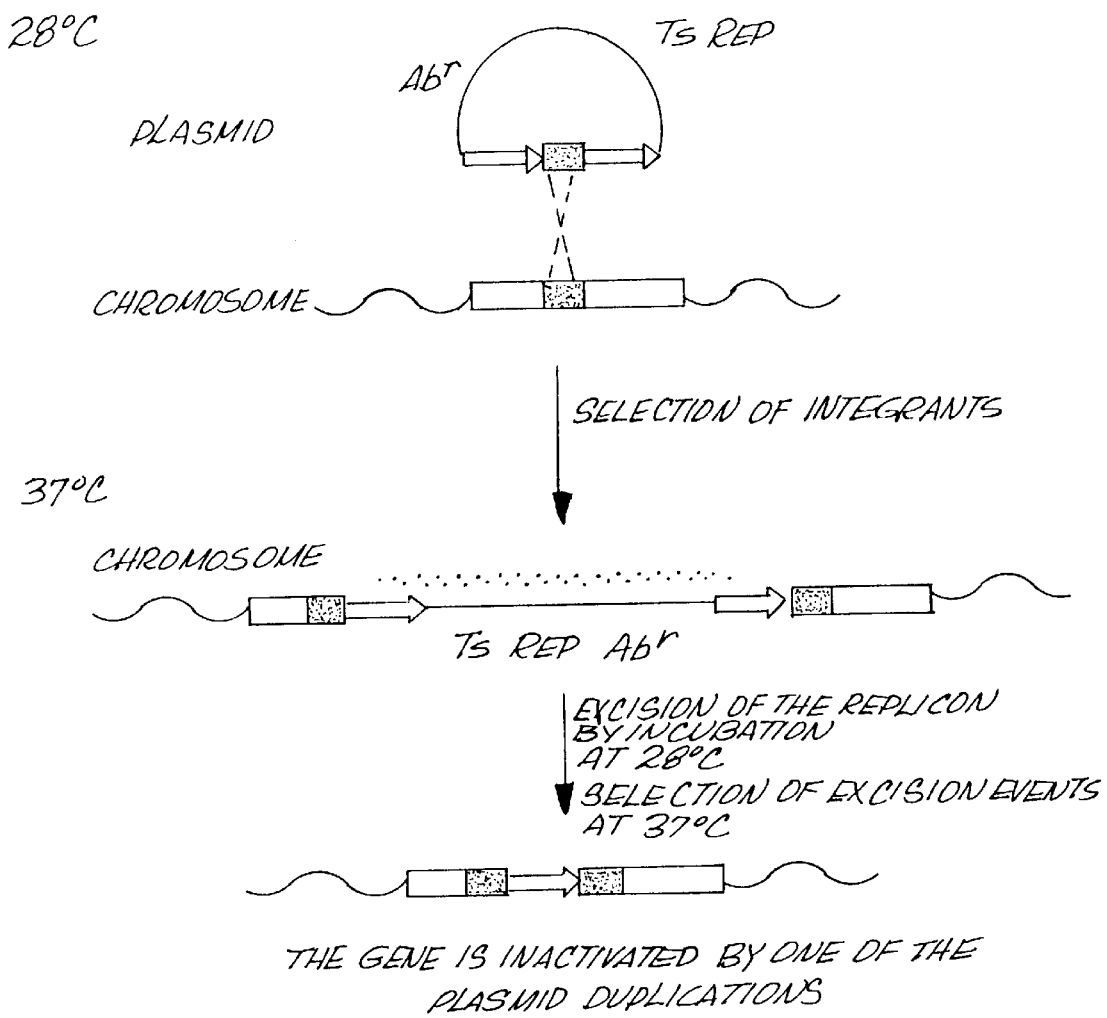

Fig. 9-1 pghost4.seq        length : 3792

```
   1  CGATTCACAA  AAAATAGGCA  CACGAAAAAC  AAGTTAAGGG  ATGCAGTTTA
  51  TGCATCCCTT  AACTTACTTA  TTAAATAATT  TATAGCTATT  GAAAAGAGAT
 101  AAGAATTGTT  CAAAGCTAAT  ATTGTTTAAA  TCGTCAATTC  CTGCATGTTT
 151  TAAGGAATTG  TTAAATTGAT  TTTTTGTAAA  TATTTTCTTG  TATTCTTTGT
 201  TAACCCATTT  CATAACGAAA  TAATTATACT  TTTGTTTATC  TTTGTGTGAT
 251  ATTCTTGATT  TTTTTCTACT  TAATCTGATA  AGTGAGCTAT  TCACTTTAGG
 301  TTTAGGATGA  AAATATTCTC  TTGGAACCAT  ACTTAATATA  GAAATATCAA
 351  CTTCTGCCAT  TAAAAGTAAT  GCCAATGAGC  GTTTTGTATT  TAATAATCTT
 401  TTAGCAAACC  CGTATTCCAC  GATTAAATAA  ATCTCATTAG  CTATACTATC
 451  AAAAACAATT  TTGCGTATTA  TATCCGTACT  TATGTTATAA  GGTATATTAC
 501  CATATATTTT  ATAGGATTGG  TTTTTAGGAA  ATTTAAACTG  CAATATATCC
 551  TTGTTTAAAA  CTTGGAAATT  ATCGTGATCA  ACAAGTTTAT  TTTCTGTAGT
 601  TTTGCATAAT  TTATGGTCTA  TTTCAATGGC  AGTTACGAAA  TTACACCTCT
 651  TTACTAATTC  AAGGGTAAAA  TGGCCTTTTC  CTGAGCCGAT  TTCAAAGATA
 701  TTATCATGTT  CATTTAATCT  TATATTTGTC  ATTATTTTAT  CTATATTATG
 751  TTTTGAAGTA  ATAAAGTTTT  GACTGTGTTT  TATATTTTTC  TCGTTCATTA
 801  TAACCCTCTT  TAATTTGGTT  ATATGAATTT  TGCTTATTAA  CGATTCATTA
 851  TAACCACTTA  TTTTTTGTTT  GGTTGATAAT  GAACTGTGCT  GATTACAAAA
 901  ATACTAAAAA  TGCCCATATT  TTTTCCTCCT  TATAAAATTA  GTATAATTAT
 951  AGCACGAGCT  CTGATAAATA  TGAACATGAT  GAGTGATCGT  TAAATTTATA
1001  CTGCAATCGG  ATGCGATTAT  TGAATAAAAG  ATATGAGAGA  TTTATCTAAT
1051  TTCTTTTTTC  TTGTAAAAAA  AGAAAGTTCT  TAAAGGTTTT  ATAGTTTTGG
1101  TCGTAGAGCA  CACGGTTTAA  CGACTTAATT  ACGAAGTAAA  TAAGTCTAGT
1151  GTGTTAGACT  TTATGAAATC  TATATACGTT  TATATATATT  TATTATCGCA
1201  TTTTTTATTA  AAACGTCTCA  AAATCGTTTC  TGAGACGTTT  TAGCGTTTAT
1251  TTCGTTTAGT  TATCGGCATA  ATCGTTAAAA  CAGGCGTTAT  CGTAGCGTAA
1301  AAGCCCTTGA  GCGTAGCGTG  GCTTTGCAGC  GAAGATGTTG  TCTGTTAGAT
1351  TATGAAAGCC  GATGACTGAA  TGAATAATA   AGCGCAGCGC  CCTTCTATTT
```

Fig. 9~2

```
2851  ATAAATAAAA  GCCCCCTGAC  GAAAGTCGAA  GGGGGTTTTT  ATTTTGGTTT
2901  GATGTTGCGA  TTAATAGCAA  TACAATTGCA  ATAAACAAAA  TGATCTTCCT
2951  TCAGGTTATG  ACCATCTGTG  CCAGTTCGTA  ATGTCTGGTC  AACTTTCCGA
3001  CTCTGAGAAA  CTTCTGGAAT  CGCTAGAGAA  TTTCTGGAAT  GGGATTCAGG
3051  AGTGGACAGA  ACGACACGGA  TATATAGTGG  ATGTGTCAAA  ACGCATACCA
3101  TTTTGAACGA  TGACCTCTAA  TAATTGTTAA  TCATGTTGGT  TACGTATTTA
3151  TTAACTTCTC  CTAGTATTAG  TAATTATCAT  GGCTGTCATG  GCGCATTAAC
3201  GGAATAAAGG  GTGTGCTTAA  ATCGGGCCAT  TTTGCGTAAT  AAGAAAAAGG
3251  ATTAATTATG  AGCGAATTGA  ATTAATAATA  AGGTAATAGA  TTTACATTAG
3301  AAAATGAAAG  GGGATTTTAT  GCGTGAGAAT  GTTACAGTCT  ATCCCTGGCG
3351  AAAGGGGGAT  GTGCTGCAAG  GCGATTAAGT  TGGGTAACGC  CAGGGTTTTC
3401  CCAGTCACGA  CGTTGTAAAA  CGACGGCCAG  TGAGCGCGCG  TAATACGACT
3451  CACTATAGGG  CGAATTGGGT  ACCGGCCCC   CCCTCGAGGT  CGACGGTATC
3501  GATAAGCTTG  ATATCGAATT  CCTGCAGCCC  GGGGGATCCA  CTAGTTCTAG
3551  AGCGGCCGCC  ACCGCGGTGG  AGCTCCAGCT  TTTGTTCCCT  TTAGTGAGGG
3601  TTAATTGCGC  GCTTGGCGTA  ATCATGGTCA  TAGCTGTTTC  CTGTGTGAAA
3651  TTGTTATCCG  CTCACAATTC  CACACAACAT  ACGAGCCGGA  AGCATAAAGT
3701  GTAAAGCCTG  GGGTGCCTAA  TGAGTGAGCT  AACTCACATT  AATTGCGTTG
3751  CGCTCACTGC  CCGCTTTCCA  GTCGGGAAAC  CTGTCGTGCC  AG
```

Fig. 9-3

```
1401  CGGTTGGAGG  AGGCTCAAGG  GAGTATGAGG  GAATGAAATT  CCCTCATGGG
1451  TTTGATTTTA  AAAATTGCTT  GCAATTTTGC  CGAGCGGTAG  CGCTGGAAAA
1501  TTTTTGAAAA  AAATTTGGAA  TTTGGAAAAA  AATGGGGGGA  AAGGAAGCGA
1551  ATTTTGCTTC  CGTACTACGA  CCCCCCATTA  AGTGCCGAGT  GCCAATTTTT
1601  GTGCCAAAAA  CGCTCTATCC  CAACTGGCTC  AAGGGTTTAA  GGGGTTTTTC
1651  AATCGCCAAC  GAATCGCCAA  CGTTTTCGCC  AACGTTTTTT  ATAAATCTAT
1701  ATTTAAGTAG  CTTTATTGTT  GTTTTTATGA  TTACAAAGTG  ATACACTAAC
1751  TTTATAAAAT  TATTTGATTG  GAGTTTTTTA  AATGGTGATT  TCAGAATCGA
1801  AAAAAAGAGT  TATGATTTCT  CTGACAAAAG  AGCAAGATAA  AAAATTAACA
1851  GATATGGCGA  AACAAAAAGG  TTTTTCAAAA  TCTGCGGTTG  CGGCGTTAGC
1901  TATAGAAGAA  TATGCAAGAA  AGGAATCAGA  ACAAAAAAAA  TAAGCGAAAG
1951  CTCGCGTTTT  TAGAAGGATA  CGAGTTTTCG  CTACTTGTTT  TTGATAAGGT
2001  AATTATATCA  TGGCTATTAA  AAATACTAAA  GCTAGAAATT  TTGGATTTTT
2051  ATTATATCCT  GACTCAATTC  CTAATGATTG  GAAAGAAAAA  TTAGAGAGTT
2101  TGGGCGTATC  TATGGCTGTC  AGTCCTTTAC  ACGATATGGA  CGAAAAAAAA
2151  GATAAAGATA  CATGGAATAA  TAGTAATATT  ATACAAAATG  GAAAGCACTA
2201  TAAAAAACCA  CACTATCACG  TTATATATAT  TGCACGAAAT  CCTGTAACAA
2251  TAGAAAGCGT  TAGGAACAAG  ATTAAGCGAA  AATTGGGGAA  TAGTTCAGTT
2301  GCTCATGTTG  AGATACTTGA  TTATATCAAA  GGTTCATATG  AATATTTGAC
2351  TCATGAATCA  AAGGACGCTA  TTGCTAAGAA  TAAACATATA  TACGACAAAA
2401  AAGATATTTT  GAACATTAAT  GATTTTGATA  TTGACCGCTA  TATAACACTT
2451  GATGAAAGCC  AAAAAGAGA   ATTGAAGAAT  TTACTTTTAG  ATATAGTGGA
2501  TGACTATAAT  TTGGTAAATA  CAAAAGATTT  AATGGCTTTT  ATTCGCCTTA
2551  GGGGAGCGGA  GTTTGGAATT  TTAAATACGA  ATGATGTAAA  AGATATTGTT
2601  TCAACAAACT  CTAGCGCCTT  TAGATTATGG  TTTGAGGGCA  ATTATCAGTG
2651  TGGATATAGA  GCAAGTTATG  CAAAGGTTCT  TGATGCTGAA  ACGGGGGAAA
2701  TAAAATGACA  AACAAAGAAA  AAGAGTTATT  TGCTGAAAAT  GAGGAATTAA
2751  AAAAAGAAAT  TAAGGACTTA  AAAGAGCGTA  TTGAAAGATA  CAGAGAAATG
2801  GAAGTTGAAT  TAAGTACAAC  AATAGATTTA  TTGAGAGGAG  GGATTATTGA
```

Fig. 10-1 pghost5.seq  length : 5284
Length: 5234

```
   1 AGGCACACGA AAAACAAGTT AAGGGATGCA GTTTA                   >seqed
                                            (included) of: pbr322.seq check: 5483 from: 1426
                                            to 2886>                 TCGGG CAGCGTTGGG
  51 TCCTGGCCAC GGGTGCGCAT GATCGTGCTC CTGTCGTTGA GGACCCGGCT
 101 AGGCTGGCGG GGTTGCCTTA CTGGTTAGCA GAATGAATCA CCGATACGCG
 151 AGCGAACGTG AAGCGACTGC TGCTGCAAAA CGTCTGCGAC CTGAGCAACA
 201 ACATGAATGG TCTTCGGTTT CCGTGTTTCG TAAAGTCTGG AAACGCGGAA
 251 GTCAGCGCCC TGCACCATTA TGTTCCGGAT CTGCATCGCA GGATGCTGCT
 301 GGCTACCCTG TGGAACACCT ACATCTGTAT TAACGAAGCG CTGGCATTGA
 351 CCCTGAGTGA TTTTTCTCTG GTCCGCCGC  ATCCATACCG CCAGTTGTTT
 401 ACCCTCACAA CGTTCCAGTA ACCGGGCATG TTCATCATCA GTAACCCGTA
 451 TCGTGAGCAT CCTCTCTCGT TTCATCGGTA TCATTACCCC CATGAACAGA
 501 AATCCCCCTT ACACGGAGGC ATCAGTGACC AAACAGGAAA AAACCGCCCT
 551 TAACATGGCC CGCTTTATCA GAAGCCAGAC ATTAACGCTT CTGGAGAAAC
 601 TCAACGAGCT GGACGCGGAT GAACAGGCAG ACATCTGTGA ATCGCTTCAC
 651 GACCACGCTG ATGAGCTTTA CCGCAGCTGC CTCGCGCGTT TCGGTGATGA
 701 CGGTGAAAAC CTCTGACACA TGCAGCTCCC GGAGACGGTC ACAGCTTGTC
 751 TGTAAGCGGA TGCCGGGAGC AGACAAGCCC GTCAGGGCGC GTCAGCGGGT
 801 GTTGGCGGGT GTCGGGGCGC AGCCATGACC CAGTCACGTA GCGATAGCGG
 851 AGTGTATACT GGCTTAACTA TGCGGCATCA GAGCAGATTG TACTGAGAGT
 901 GCACCATATG CGGTGTGAAA TACCGCACAG ATGCGTAAGG AGAAAATACC
 951 GCATCAGGCG CTCTTCCGCT TCCTCGCTCA CTGACTCGCT GCGCTCGGTC
1001 GTTCGGCTGC GGCGAGCGGT ATCAGCTCAC TCAAAGGCGG TAATACGGTT
1051 ATCCACAGAA TCAGGGGATA ACGCAGGAAA GAACATGTGA GCAAAAGGCC
1101 AGCAAAAGGC CAGGAACCGT AAAAAGGCCG CGTTGCTGGC GTTTTTCCAT
1151 AGGCTCCGCC CCCTGACGA  GCATCACAAA AATCGACGCT CAAGTCAGAG
1201 GTGGCGAAAC CCGACAGGAC TATAAAGATA CCAGGCGTTT CCCCCTGGAA
```

*Fig.10-2*

```
1251 GCTCCCTCGT GCGCTCTCCT GTTCCGACCC TGCCGCTTAC CGGATACCTG
1301 TCCGCCTTTC TCCCTTCGGG AAGCGTGGCG CTTTCTCATA GCTCACGCTG
1351 TAGGTATCTC AGTTCGGTGT AGGTCGTTCG CTCCAAGCTG GGCTGTGTGC
1401 ACGAACCCCC CGTTCAGCCC GACCGCTGCG CCTTATCCGG TAACTATCGT
1451 CTTGAGTCCA ACCCGGTAAG ACACGACTTA TCGCCACTGG CAGCAG<seq
``` ed (included) of: pbr322.seq check: 5483 from: 1426
to: 2886>

TCCC

```
1501 TTAACTTACT TATTAAATAA TTTATAGCTA TTGAAAAGAG ATAAGAATTG
1551 TTCAAAGCTA ATATTGTTTA AATCGTCAAT TCCTGCATGT TTTAAGGAAT
1601 TGTTAAATTG ATTTTTTGTA AATATTTCT TGTATTCTTT GTTAACCCAT
1651 TTCATAACGA AATAATTATA CTTTTGTTTA TCTTTGTGTG ATATTCTTGA
1701 TTTTTTTCTA CTTAATCTGA TAAGTGAGCT ATTCACTTTA GGTTTAGGAT
1751 GAAAATATTC TCTTGGAACC ATACTTAATA TAGAAATATC AACTTCTGCC
1801 ATTAAAGTA ATGCCAATGA GCGTTTTGTA TTTAATAATC TTTTAGCAAA
1851 CCCGTATTCC ACGATTAAAT AAATCTCATT AGCTATACTA TCAAAACAA
1901 TTTTGCGTAT TATATCCGTA CTTATGTTAT AAGGTATATT ACCATATATT
1951 TTATAGGATT GGTTTTTAGG AAATTTAAAC TGCAATATAT CCTTGTTTAA
2001 AACTTGGAAA TTATCGTGAT CAACAAGTTT ATTTTCTGTA GTTTTGCATA
2051 ATTTATGGTC TATTTCAATG GCAGTTACGA AATTACACCT CTTTACTAAT
2101 TCAAGGGTAA AATGGCCTTT TCCTGAGCCG ATTTCAAAGA TATTATCATG
2151 TTCATTTAAT CTTATATTTG TCATTATTTT ATCTATATTA TGTTTTGAAG
2201 TAATAAAGTT TTGACTGTGT TTTATATTTT TCTCGTTCAT TATAACCCTC
2251 TTTAATTTGG TTATATGAAT TTTGCTTATT AACGATTCAT TATAACCACT
2301 TATTTTTTGT TTGGTTGATA ATGAACTGTG CTGATTACAA AAATACTAAA
2351 AATGCCCATA TTTTTTCCTC CTTATAAAAT TAGTATAATT ATAGCACGAG
2401 CTCTGATAAA TATGAACATG ATGAGTGATC GTTAAATTTA TACTGCAATC
2451 GGATGCGATT ATTGAATAAA AGATATGAGA GATTTATCTA ATTTCTTTTT
2501 TCTTGTAAAA AAAGAAAGTT CTTAAAGGTT TTATAGTTTT GGTCGTAGAG
2551 CACACGGTTT AACGACTTAA TTACGAAGTA AATAAGTCTA GTGTGTTAGA
```

Fig. 10-3

```
2601  CTTTATGAAA  TCTATATACG  TTTATATATA  TTTATTATC
                                                   >SEQED
      (included) of: pwv01. check: 7166 from: 1 to: 1744>
                                                 C GATTTTTTAT
2651  TAAAACGTCT  CAAAATCGTT  TCTGAGACGT  TTTAGCGTTT  ATTTCGTTTA
2701  GTTATCGGCA  TAATCGTTAA  AACAGGCGTT  ATCGTAGCGT  AAAAGCCCTT
2751  GAGCGTAGCG  TGGCTTTGCA  GCGAAGATGT  TGTCTGTTAG  ATTATGAAAG
2801  CCGATGACTG  AATGAAATAA  TAAGCGCAGC  GCCCTTCTAT  TTCGGTTGGA
2851  GGAGGCTCAA  GGGAGTATGA  GGGAATGAAA  TTCCCTCATG  GGTTTGATTT
2901  TAAAAATTGC  TTGCAATTTT  GCCGAGCGGT  AGCGCTGGAA  AATTTTTGAA
2951  AAAAATTTGG  AATTTGGAAA  AAATGGGGG   GAAAGGAAGC  GAATTTTGCT
3001  TCCGTACTAC  GACCCCCCAT  TAAGTGCCGA  GTGCCAATTT  TTGTGCCAAA
3051  AACGCTCTAT  CCCAACTGGC  TCAAGGGTTT  AAGGGGTTTT  TCAATCGCCA
3101  ACGAATCGCC  AACGTTTTCG  CCAACGTTTT  TTATAAATCT  ATATTTAAGT
3151  AGCTTTATTG  TTGTTTTTAT  GATTACAAAG  TGATACACTA  ACTTTATAAA
3201  ATTATTTGAT  TGGAGTTTTT  TAAATGGTGA  TTTCAGAATC  GAAAAAAGA
3251  GTTATGATTT  CTCTGACAAA  AGAGCAAGAT  AAAAAATTAA  CAGATATGGC
3301  GAAACAAAAA  GGTTTTCAA   AATCTGCGGT  TGCGGCGTTA  GCTATAGAAG
3351  AATATGCAAG  AAAGGAATCA  GAACAAAAAA  AATAAGCGAA  AGCTCGCGTT
3401  TTTAGAAGGA  TACGAGTTTT  CGCTACTTGT  TTTTGATAAG  GTAATTATAT
3451  CATGGCTATT  AAAAATACTA  AAGCTAGAAA  TTTTGGATTT  TTATTATATC
3501  CTGACTCAAT  TCCTAATGAT  TGGAAAGAAA  AATTAGAGAG  TTTGGGCGTA
3551  TCTATGGCTG  TCAGTCCTTT  ACACGATATG  GACGAAAAAA  AAGATAAAGA
3601  TACATGGAAT  AATAGTAATA  TTATACAAAA  TGGAAAGCAC  TATAAAAAAC
3651  CACACTATCA  CGTTATATAT  ATTGCACGAA  ATCCTGTAAC  AATAGAAAGC
3701  GTTAGGAACA  AGATTAAGCG  AAAATTGGGG  AATAGTTCAG  TTGCTCATGT
3751  TGAGATACTT  GATTATATCA  AAGGTTCATA  TGAATATTTG  ACTCATGAAT
3801  CAAAGGACGC  TATTGCTAAG  AATAAACATA  TATACGACAA  AAAAGATATT
3851  TTGAACATTA  ATGATTTTGA  TATTGACCGC  TATATAACAC  TTGATGAAAG
3901  CCAAAAAAGA  GAATTGAAGA  ATTTACTTTT  AGATATAGTG  GATGACTATA
3951  ATTTGGTAAA  TACAAAAGAT  TTAATGGCTT  TTATTCGCCT  TAGGGGAGCG
```

Fig. 10-4

```
4001  GAGTTTGGAA  TTTTAAATAC  GAATGATGTA  AAAGATATTG  TTTCAACAAA
4051  CTCTAGCGCC  TTTAGATTAT  GGTTTGAGGG  CAATTATCAG  TGTGGATATA
4101  GAGCAAGTTA  TGCAAAGGTT  CTTGATGCTG  AAACGGGGGA  AATAAAATGA
4151  CAAACAAAGA  AAAAGAGTTA  TTTGCTGAAA  ATGAGGAATT  AAAAAAAGAA
4201  ATTAAGGACT  TAAAAGAGCG  TATTGAAAGA  TACAGAGAAA  TGGAAGTTGA
4251  ATTAAGTACA  ACAATAGATT  TATTGAGAGG  AGGGATTATT  GAATAAATAA
4301  AAGCCCCCTG  ACGAAAGTCG  AAGGGGGTTT  TTATTTTGGT  TTGATGTTGC
4351  GATTAATAGC  AATACAATTG  CAATAAACAA  AAT
```
<SEQED (included)
of: pwv01. check: 7166 from: 1 to: 1744<
>SEQED (included)
reverse of: pub110. seq check: 5091 from: 1964
to: 2366>

```
                                                   GATCTTC  CTTCAGGTTA
4401  TGACCATCTG  TGCCAGTTCG  TAATGTCTGG  TCAACTTTCC  GACTCTGAGA
4451  AACTTCTGGA  ATCGCTAGAG  AATTTCTGGA  ATGGGATTCA  GGAGTGGACA
4501  GAACGACACG  GATATATAGT  GGATGTGTCA  AAACGCATAC  CATTTTGAAC
4551  GATGACCTCT  AATAATTGTT  AATCATGTTG  GTTACGTATT  TATTAACTTC
4601  TCCTAGTATT  AGTAATTATC  ATGGCTGTCA  TGGCGCATTA  ACGGAATAAA
4651  GGGTGTGCTT  AAATCGGGCC  ATTTTGCGTA  ATAAGAAAAA  GGATTAATTA
4701  TGAGCGAATT  GAATTAATAA  TAAGGTAATA  GATTTACATT  AGAAAATGAA
4751  AGGGGATTTT  ATGCGTGAGA  ATGTTACAGT  CTATCC
```
<SEQED
(included) reverse of: pub110. seq check: 5091
from: 1964 to: 2366<           >seqed
(included) of: pak. seq check: 8495 from: 530
to: 977>

```
                                                      CTGG  CGAAAGGGGG
4801  ATGTGCTGCA  AGGCGATTAA  GTTGGGTAAC  GCCAGGGTTT  TCCCAGTCAC
4851  GACGTTGTAA  AACGACGGCC  AGTGAGCGCG  CGTAATACGA  CTCACTATAG
4901  GGCGAATTGG  GTACCGGGCC  CCCCCTCGAG  GTCGACGGTA  TCGATAAGCT
4951  TGATATCGAA  TTCCTGCAGC  CCGGGGATC   CACTAGTTCT  AGAGCGGCCG
5001  CCACCGCGGT  GGAGCTCCAG  CTTTTGTTCC  CTTTAGTGAG  GGTTAATTGC
5051  GCGCTTGGCG  TAATCATGGT  CATAGCTGTT  TCCTGTGTGA  AATTGTTATC
5101  CGCTCACAAT  TCCACACAAC  ATACGAGCCG  GAAGCATAAA  GTGTAAAGCC
```

*Fig. 10-5*

```
5151  TGGGGTGCCT AATGAGTGAG CTAACTCACA TTAATTGCGT TGCGCTCACT
5201  GCCCGCTTTC CAGTCGGGAA ACCTGTCGTG CCAG
                                         <seqed (included)
      of: psk. seq check: 8495 from: 530 to: 977<
                                        >SEQED (included)
      of: pcl.ba check: 2015 from: 974 to: 2004>
```

*Fig. 11-1* pghost6.seq   length 6722   Type: N

```
   1 CGATTCACAA AAAATAGGCA CACGAAAAAC AAGTTAAGGG ATGCAGTTTA
  51 AATTCTTGAA GACGAAAGGG CCTCGTGATA CGCCTATTTT TATAGGTTAA
 101 TGTCATGATA ATAATGGTTT CTTAGACGTC AGGTGGCACT TTTCGGGGAA
 151 ATGTGCGCGG AACCCCTATT TGTTTATTTT TCTAAATACA TTCAAATATG
 201 TATCCGCTCA TGAGACAATA ACCCTGATAA ATGCTTCAAT AATATTGAAA
 251 AAGGAAGAGT ATGAGTATTC AACATTTCCG TGTCGCCCTT ATTCCCTTTT
 301 TTGCGGCATT TTGCCTTCCT GTTTTTGCTC ACCCAGAAAC GCTGGTGAAA
 351 GTAAAAGATG CTGAAGATCA GTTGGGTGCA CGAGTGGGTT ACATCGAACT
 401 GGATCTCAAC AGCGGTAAGA TCCTTGAGAG TTTTCGCCCC GAAGAACGTT
 451 TTCCAATGAT GAGCACTTTT AAAGTTCTGC TATGTGGCGC GGTATTATCC
 501 CGTGTTGACG CCGGGCAAGA GCAACTCGGT CGCCGCATAC ACTATTCTCA
 551 GAATGACTTG GTTGAGTACT CACCAGTCAC AGAAAAGCAT CTTACGGATG
 601 GCATGACAGT AAGAGAATTA TGCAGTGCTG CCATAACCAT GAGTGATAAC
 651 ACTGCGGCCA ACTTACTTCT GACAACGATC GGAGGACCGA AGGAGCTAAC
 701 CGCTTTTTTG CACAACATGG GGGATCATGT AACTCGCCTT GATCGTTGGG
 751 AACCGGAGCT GAATGAAGCC ATACCAAACG ACGAGCGTGA CACCACGATG
 801 CCTGCAGCAA TGGCAACAAC GTTGCGCAAA CTATTAACTG GCGAACTACT
 851 TACTCTAGCT TCCCGGCAAC AATTAATAGA CTGGATGGAG GCGGATAAAG
 901 TTGCAGGACC ACTTCTGCGC TCGGCCCTTC CGGCTGGCTG GTTTATTGCT
 951 GATAAATCTG GAGCCGGTGA GCGTGGGTCT CGCGGTATCA TTGCAGCACT
1001 GGGGCCAGAT GGTAAGCCCT CCCGTATCGT AGTTATCTAC ACGACGGGGA
1051 GTCAGGCAAC TATGGATGAA CGAAATAGAC AGATCGCTGA GATAGGTGCC
1101 TCACTGATTA AGCATTGGTA ACTGTCAGAC CAAGTTTACT CATATATACT
1151 TTAGATTGAT TTAAAACTTC ATTTTTAATT TAAAAGGATC TAGGTGAAGA
1201 TCCTTTTTGA TAATCTCATG ACCAAAATCC CTTAACGTGA GTTTTCGTTC
1251 CACTGAGCGT CAGACCCCGT AGAAAAGATC AAAGGATCTT CTTGAGATCC
1301 TTTTTTTCTG CGCGTAATCT GCTGCTTGCA AACAAAAAAA CCACCGCTAC
1351 CAGCGGTGGT TTGTTTGCCG GATCAAGAGC TACCAACTCT TTTTCCGAAG
```

Fig. 11-2

```
1401  GTAACTGGCT  TCAGCAGAGC  GCAGATACCA  AATACTGTCC  TTCTAGTGTA
1451  GCCGTAGTTA  GGCCACCACT  TCAAGAACTC  TGTAGCACCG  CCTACATACC
1501  TCGCTCTGCT  AATCCTGTTA  CCAGTGGCTG  CTGCCAGTGG  CGATAAGTCG
1551  TGTCTTACCG  GGTTGGACTC  AAGACGATAG  TTACCGGATA  AGGCGCAGCG
1601  GTCGGGCTGA  ACGGGGGGTT  CGTGCACACA  GCCCAGCTTG  GAGCGAACGA
1651  CCTACACCGA  ACTGAGATAC  CTACAGCGTG  AGCTATGAGA  AAGCGCCACG
1701  CTTCCCGAAG  GGAGAAAGGC  GGACAGGTAT  CCGGTAAGCG  GCAGGGTCGG
1751  AACAGGAGAG  CGCACGAGGG  AGCTTCCAGG  GGGAAACGCC  TGGTATCTTT
1801  ATAGTCCTGT  CGGGTTTCGC  CACCTCTGAC  TTGAGCGTCG  ATTTTTGTGA
1851  TGCTCGTCAG  GGGGGCGGAG  CCTATGGAAA  AACGCCAGCA  ACGCGGCCTT
1901  TTTACGGTTC  CTGGCCTTTT  GCTGGCCTTT  TGCTCACATG  TTCTTTCCTG
1951  CGTTATCCCC  TGATTCTGTG  GATAACCGTA  TTACCGCCTT  TGAGTGAGCT
2001  GATACCGCTC  GCCGCAGCCG  AACGACCGAG  CGCAGCGAGT  CAGTGAGCGA
2051  GGAAGCGGAA  GAGCGCCTGA  TGCGGTATTT  TCTCCTTACG  CATCTGTGCG
2101  GTATTTCACA  CCGCATATGG  TGCACTCTCA  GTACAATCTG  CTCTGATGCC
2151  GCATAGTTAA  GCCAGTATAC  ACTCCGCTAT  CGCTACGTGA  CTGGGTCATG
2201  GCTGCGCCCC  GACACCCGCC  AACACCCGCT  GACGCGCCCT  GACGGGCTTG
2251  TCTGCTCCCG  GCATCCGCTT  ACAGACAAGC  TGTGACCGTC  TCCGGGAGCT
2301  GCATGTGTCA  GAGGTTTTCA  CCGTCATCAC  CGAAACGCGC  GAGGCAGCTG
2351  CGGTAAAGCT  CATCAGCGTG  GTCGTGAAGC  GATTCACAGA  TGTCTGCCTG
2401  TTCATCCGCG  TCCAGCTCGT  TGAGTTTCTC  CAGAAGCGTT  AATGTCTGGC
2451  TTCTGATAAA  GCGGGCCATG  TTAAGGGCGG  TTTTTTCCTG  TTTGGTCACT
2501  GATGCCTCCG  TGTAAGGGGG  ATTTCTGTTC  ATGGGGGTAA  TGATACCGAT
2551  GAAACGAGAG  AGGATGCTCA  CGATACGGGT  TACTGATGAT  GAACATGCCC
2601  GGTTACTGGA  ACGTTGTGAG  GGTAAACAAC  TGGCGGTATG  GATGCGGCGG
2651  GACCAGAGAA  AAATCACTCA  GGGTCAATGC  CAGCGCTTCG  TTAATACAGA
2701  TGTAGGTGTT  CCACAGGGTA  GCCAGCAGCA  TCCTGCGATG  CAGATCCGGA
2751  ACATAATGGT  GCAGGGCGCT  GACTTCCGCG  TTTCCAGACT  TTACGAAACA
2801  CGGAAACCGA  AGACCATTCA  TGTTGTTGCT  CAGGTCGCAG  ACGTTTTGCA
```

Fig. 11-3

```
2851  GCAGCAGTCG  CTTCACGTTC  GCTCGCGTAT  CGGTGATTCA  TTCTGCTAAC
2901  CAGTAAGGCA  ACCCCGCCAG  CCTAGCCGGG  TCCTCAACGA  CAGGAGCACG
2951  ATCATGCGCA  CCCGTGGCCA  GGACCCAACG  CTGCTCCCTT  AACTTACTTA
3001  TTAAATAATT  TATAGCTATT  GAAAAGAGAT  AAGAATTGTT  CAAAGCTAAT
3051  ATTGTTTAAA  TCGTCAATTC  CTGCATGTTT  TAAGGAATTG  TTAAATTGAT
3101  TTTTTGTAAA  TATTTTCTTG  TATTCTTTGT  TAACCCATTT  CATAACGAAA
3151  TAATTATACT  TTTGTTTATC  TTTGTGTGAT  ATTCTTGATT  TTTTTCTACT
3201  TAATCTGATA  AGTGAGCTAT  TCACTTTAGG  TTTAGGATGA  AAATATTCTC
3251  TTGGAACCAT  ACTTAATATA  GAAATATCAA  CTTCTGCCAT  TAAAAGTAAT
3301  GCCAATGAGC  GTTTTGTATT  TAATAATCTT  TTAGCAAACC  CGTATTCCAC
3351  GATTAAATAA  ATCTCATTAG  CTATACTATC  AAAAACAATT  TTGCGTATTA
3401  TATCCGTACT  TATGTTATAA  GGTATATTAC  CATATATTTT  ATAGGATTGG
3451  TTTTTAGGAA  ATTTAAACTG  CAATATATCC  TTGTTTAAAA  CTTGGAAATT
3501  ATCGTGATCA  ACAAGTTTAT  TTTCTGTAGT  TTTGCATAAT  TTATGGTCTA
3551  TTTCAATGGC  AGTTACGAAA  TTACACCTCT  TTACTAATTC  AAGGGTAAAA
3601  TGGCCTTTTC  CTGAGCCGAT  TTCAAAGATA  TTATCATGTT  CATTTAATCT
3651  TATATTTGTC  ATTATTTTAT  CTATATTATG  TTTTGAAGTA  ATAAAGTTTT
3701  GACTGTGTTT  TATATTTTTC  TCGTTCATTA  TAACCCTCTT  TAATTTGGTT
3751  ATATGAATTT  TGCTTATTAA  CGATTCATTA  TAACCACTTA  TTTTTTGTTT
3801  GGTTGATAAT  GAACTGTGCT  GATTACAAAA  ATACTAAAAA  TGCCCATATT
3851  TTTTCCTCCT  TATAAAATTA  GTATAATTAT  AGCACGAGCT  CTGATAAATA
3901  TGAACATGAT  GAGTGATCGT  TAAATTTATA  CTGCAATCGG  ATGCGATTAT
3951  TGAATAAAAG  ATATGAGAGA  TTTATCTAAT  TTCTTTTTTC  TTGTAAAAAA
4001  AGAAAGTTCT  TAAAGGTTTT  ATAGTTTTGG  TCGTAGAGCA  CACGGTTTAA
4051  CGACTTAATT  ACGAAGTAAA  TAAGTCTAGT  GTGTTAGACT  TTATGAAATC
4101  TATATACGTT  TATATATATT  TATTATCCGA  TTTTTTATTA  AAACGTCTCA
4151  AAATCGTTTC  TGAGACGTTT  TAGCGTTTAT  TTCGTTTAGT  TATCGGCATA
4201  ATCGTTAAAA  CAGGCGTTAT  CGTAGCGTAA  AAGCCCTTGA  GCGTAGCGTG
4251  GCTTTGCAGC  GAAGATGTTG  TCTGTTAGAT  TATGAAAGCC  GATGACTGAA
```

Fig. 11-4

```
4301  TGAAATAATA  AGCGCAGCGC  CCTTCTATTT  CGGTTGGAGG  AGGCTCAAGG
4351  GAGTATGAGG  GAATGAAATT  CCCTCATGGG  TTTGATTTTA  AAAATTGCTT
4401  GCAATTTTGC  CGAGCGGTAG  CGCTGGAAAA  TTTTTGAAAA  AAATTTGGAA
4451  TTTGGAAAAA  AATGGGGGGA  AAGGAAGCGA  ATTTTGCTTC  CGTACTACGA
4501  CCCCCCATTA  AGTGCCGAGT  GCCAATTTTT  GTGCCAAAAA  CGCTCTATCC
4551  CAACTGGCTC  AAGGGTTTAA  GGGGTTTTTC  AATCGCCAAC  GAATCGCCAA
4601  CGTTTTCGCC  AACGTTTTTT  ATAAATCTAT  ATTTAAGTAG  CTTTATTGTT
4651  GTTTTTATGA  TTACAAAGTG  ATACACTAAC  TTTATAAAAT  TATTTGATTG
4701  GAGTTTTTTA  AATGGTGATT  TCAGAATCGA  AAAAAGAGT   TATGATTTCT
4751  CTGACAAAAG  AGCAAGATAA  AAAATTAACA  GATATGGCGA  AACAAAAAGG
4801  TTTTTCAAAA  TCTGCGGTTG  CGGCGTTAGC  TATAGAAGAA  TATGCAAGAA
4851  AGGAATCAGA  ACAAAAAAAA  TAAGCGAAAG  CTCGCGTTTT  TAGAAGGATA
4901  CGAGTTTTCG  CTACTTGTTT  TTGATAAGGT  AATTATATCA  TGGCTATTAA
4951  AAATACTAAA  GCTAGAAATT  TTGGATTTTT  ATTATATCCT  GACTCAATTC
5001  CTAATGATTG  GAAAGAAAAA  TTAGAGAGTT  TGGGCGTATC  TATGGCTGTC
5051  AGTCCTTTAC  ACGATATGGA  CGAAAAAAAA  GATAAAGATA  CATGGAATAA
5101  TAGTAATATT  ATACAAAATG  GAAAGCACTA  TAAAAAACCA  CACTATCACG
5151  TTATATATAT  TGCACGAAAT  CCTGTAACAA  TAGAAAGCGT  TAGGAACAAG
5201  ATTAAGCGAA  AATTGGGGAA  TAGTTCAGTT  GCTCATGTTG  AGATACTTGA
5251  TTATATCAAA  GGTTCATATG  AATATTTGAC  TCATGAATCA  AAGGACGCTA
5301  TTGCTAAGAA  TAAACATATA  TACGACAAAA  AAGATATTTT  GAACATTAAT
5351  GATTTTGATA  TTGACCGCTA  TATAACACTT  GATGAAAGCC  AAAAAAGAGA
5401  ATTGAAGAAT  TTACTTTTAG  ATATAGTGGA  TGACTATAAT  TTGGTAAATA
5451  CAAAAGATTT  AATGGCTTTT  ATTCGCCTTA  GGGGAGCGGA  GTTTGGAATT
5501  TTAAATACGA  ATGATGTAAA  AGATATTGTT  TCAACAAACT  CTAGCGCCTT
5551  TAGATTATGG  TTTGAGGGCA  ATTATCAGTG  TGGATATAGA  GCAAGTTATG
5601  CAAAGGTTCT  TGATGCTGAA  ACGGGGGAAA  TAAAATGACA  AACAAAGAAA
5651  AAGAGTTATT  TGCTGAAAAT  GAGGAATTAA  AAAAGAAAT   TAAGGACTTA
5701  AAAGAGCGTA  TTGAAAGATA  CAGAGAAATG  GAAGTTGAAT  TAAGTACAAC
```

Fig. 11-5

| | | | | |
|---|---|---|---|---|
| 5751 AATAGATTTA | TTGAGAGGAG | GGATTATTGA | ATAAATAAAA | GCCCCCTGAC |
| 5801 GAAAGTCGAA | GGGGGTTTTT | ATTTTGGTTT | GATGTTGCGA | TTAATAGCAA |
| 5851 TACAATTGCA | ATAAACAAAA | TGATCTTCCT | TCAGGTTATG | ACCATCTGTG |
| 5901 CCAGTTCGTA | ATGTCTGGTC | AACTTTCCGA | CTCTGAGAAA | CTTCTGGAAT |
| 5951 CGCTAGAGAA | TTTCTGGAAT | GGGATTCAGG | AGTGGACAGA | ACGACACGGA |
| 6001 TATATAGTGG | ATGTGTCAAA | ACGCATACCA | TTTTGAACGA | TGACCTCTAA |
| 6051 TAATTGTTAA | TCATGTTGGT | TACGTATTTA | TTAACTTCTC | CTAGTATTAG |
| 6101 TAATTATCAT | GGCTGTCATG | GCGCATTAAC | GGAATAAAGG | GTGTGCTTAA |
| 6151 ATCGGGCCAT | TTTGCGTAAT | AAGAAAAAGG | ATTAATTATG | AGCGAATTGA |
| 6201 ATTAATAATA | AGGTAATAGA | TTTACATTAG | AAAATGAAAG | GGGATTTTAT |
| 6251 GCGTGAGAAT | GTTACAGTCT | ATCCCTGGCG | AAAGGGGGAT | GTGCTGCAAG |
| 6301 GCGATTAAGT | TGGGTAACGC | CAGGGTTTTC | CCAGTCACGA | CGTTGTAAAA |
| 6351 CGACGGCCAG | TGAGCGCGCG | TAATACGACT | CACTATAGGG | CGAATTGGGT |
| 6401 ACCGGGCCCC | CCCTCGAGGT | CGACGGTATC | GATAAGCTTG | ATATCGAATT |
| 6451 CCTGCAGCCC | GGGGGATCCA | CTAGTTCTAG | AGCGGCCGCC | ACCGCGGTGG |
| 6501 AGCTCCAGCT | TTTGTTCCCT | TTAGTGAGGG | TTAATTGCGC | GCTTGGCGTA |
| 6551 ATCATGGTCA | TAGCTGTTTC | CTGTGTGAAA | TTGTTATCCG | CTCACAATTC |
| 6601 CACACAACAT | ACGAGCCGGA | AGCATAAAGT | GTAAAGCCTG | GGGTGCCTAA |
| 6651 TGAGTGAGCT | AACTCACATT | AATTGCGTTG | CGCTCACTGC | CCGCTTTCCA |
| 6701 GTCGGGAAAC | CTGTCGTGCC | AG | | |

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 3792 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
CGATTCACAA AAAATAGGCA CACGAAAAAC AAGTTAAGGG ATGCAGTTTA TGCATCCCTT      60

AACTTACTTA TTAAATAATT TATAGCTATT GAAAAGAGAT AAGAATTGTT CAAAGCTAAT     120

ATTGTTTAAA TCGTCAATTC CTGCATGTTT TAAGGAATTG TTAAATTGAT TTTTTGTAAA     180

TATTTTCTTG TATTCTTTGT TAACCCATTT CATAACGAAA TAATTATACT TTTGTTTATC     240

TTTGTGTGAT ATTCTTGATT TTTTTCTACT TAATCTGATA AGTGAGCTAT TCACTTTAGG     300

TTTAGGATGA AAATATTCTC TTGGAACCAT ACTTAATATA GAAATATCAA CTTCTGCCAT     360

TAAAAGTAAT GCCAATGAGC GTTTTGTATT TAATAATCTT TTAGCAAACC CGTATTCCAC     420

GATTAAATAA ATCTCATTAG CTATACTATC AAAAACAATT TTGCGTATTA TATCCGTACT     480

TATGTTATAA GGTATATTAC CATATATTTT ATAGGATTGG TTTTTAGGAA ATTTAAACTG     540

CAATATATCC TTGTTTAAAA CTTGGAAATT ATCGTGATCA ACAAGTTTAT TTTCTGTAGT     600

TTTGCATAAT TTATGGTCTA TTTCAATGGC AGTTACGAAA TTACACCTCT TTACTAATTC     660

AAGGGTAAAA TGGCCTTTTC CTGAGCCGAT TTCAAAGATA TTATCATGTT CATTTAATCT     720

TATATTTGTC ATTATTTTAT CTATATTATG TTTTGAAGTA ATAAAGTTTT GACTGTGTTT     780

TATATTTTTC TCGTTCATTA TAACCCTCTT TAATTTGGTT ATATGAATTT TGCTTATTAA     840

CGATTCATTA TAACCACTTA TTTTTTGTTT GGTTGATAAT GAACTGTGCT GATTACAAAA     900

ATACTAAAAA TGCCCATATT TTTTCCTCCT TATAAAATTA GTATAATTAT AGCACGAGCT     960

CTGATAAATA TGAACATGAT GAGTGATCGT TAAATTTATA CTGCAATCGG ATGCGATTAT    1020

TGAATAAAAG ATATGAGAGA TTTATCTAAT TTCTTTTTTC TTGTAAAAAA AGAAAGTTCT    1080

TAAAGGTTTT ATAGTTTTGG TCGTAGAGCA CACGGTTTAA CGACTTAATT ACGAAGTAAA    1140

TAAGTCTAGT GTGTTAGACT TTATGAAATC TATATACGTT TATATATATT TATTATCGCA    1200

TTTTTTATTA AAACGTCTCA AAATCGTTTC TGAGACGTTT TAGCGTTTAT TTCGTTTAGT    1260

TATCGGCATA ATCGTTAAAA CAGGCGTTAT CGTAGCGTAA AAGCCCTTGA GCGTAGCGTG    1320

GCTTTGCAGC GAAGATGTTG TCTGTTAGAT TATGAAAGCC GATGACTGAA TGAAATAATA    1380

AGCGCAGCGC CCTTCTATTT CGGTTGGAGG AGGCTCAAGG GAGTATGAGG GAATGAAATT    1440

CCCTCATGGG TTTGATTTTA AAAATTGCTT GCAATTTTGC CGAGCGGTAG CGCTGGAAAA    1500
```

-continued

```
TTTTTGAAAA AAATTTGGAA TTTGGAAAAA AATGGGGGA AAGGAAGCGA ATTTTGCTTC      1560

CGTACTACGA CCCCCCATTA AGTGCCGAGT GCCAATTTTT GTGCCAAAAA CGCTCTATCC      1620

CAACTGGCTC AAGGGTTTAA GGGGTTTTTC AATCGCCAAC GAATCGCCAA CGTTTTCGCC      1680

AACGTTTTTT ATAAATCTAT ATTTAAGTAG CTTTATTGTT GTTTTTATGA TTACAAAGTG      1740

ATACACTAAC TTTATAAAAT TATTTGATTG GAGTTTTTTA AATGGTGATT TCAGAATCGA      1800

AAAAAAGAGT TATGATTTCT CTGACAAAAG AGCAAGATAA AAAATTAACA GATATGGCGA      1860

AACAAAAAGG TTTTTCAAAA TCTGCGGTTG CGGCGTTAGC TATAGAAGAA TATGCAAGAA      1920

AGGAATCAGA ACAAAAAAAA TAAGCGAAAG CTCGCGTTTT TAGAAGGATA CGAGTTTTCG      1980

CTACTTGTTT TTGATAAGGT AATTATATCA TGGCTATTAA AAATACTAAA GCTAGAAATT      2040

TTGGATTTTT ATTATATCCT GACTCAATTC CTAATGATTG GAAAGAAAAA TTAGAGAGTT      2100

TGGGCGTATC TATGGCTGTC AGTCCTTTAC ACGATATGGA CGAAAAAAAA GATAAAGATA      2160

CATGGAATAA TAGTAATATT ATACAAATG GAAAGCACTA TAAAAAACCA CACTATCACG      2220

TTATATATAT TGCACGAAAT CCTGTAACAA TAGAAAGCGT TAGGAACAAG ATTAAGCGAA      2280

AATTGGGGAA TAGTTCAGTT GCTCATGTTG AGATACTTGA TTATATCAAA GGTTCATATG      2340

AATATTTGAC TCATGAATCA AAGGACGCTA TTGCTAAGAA TAAACATATA TACGACAAAA      2400

AAGATATTTT GAACATTAAT GATTTTGATA TTGACCGCTA TATAACACTT GATGAAAGCC      2460

AAAAAAGAGA ATTGAAGAAT TTACTTTTAG ATATAGTGGA TGACTATAAT TTGGTAAATA      2520

CAAAAGATTT AATGGCTTTT ATTCGCCTTA GGGGAGCGGA GTTTGGAATT TTAAATACGA      2580

ATGATGTAAA AGATATTGTT TCAACAAACT CTAGCGCCTT TAGATTATGG TTTGAGGGCA      2640

ATTATCAGTG TGGATATAGA GCAAGTTATG CAAAGGTTCT TGATGCTGAA ACGGGGAAA      2700

TAAAATGACA AACAAAGAAA AAGAGTTATT TGCTGAAAAT GAGGAATTAA AAAAAGAAAT      2760

TAAGGACTTA AAAGAGCGTA TTGAAAGATA CAGAGAAATG GAAGTTGAAT TAAGTACAAC      2820

AATAGATTTA TTGAGAGGAG GGATTATTGA ATAAATAAAA GCCCCCTGAC GAAAGTCGAA      2880

GGGGGTTTTT ATTTTGGTTT GATGTTGCGA TTAATAGCAA TACAATTGCA ATAAACAAAA      2940

TGATCTTCCT TCAGGTTATG ACCATCTGTG CCAGTTCGTA ATGTCTGGTC AACTTTCCGA      3000

CTCTGAGAAA CTTCTGGAAT CGCTAGAGAA TTTCTGGAAT GGGATTCAGG AGTGGACAGA      3060

ACGACACGGA TATATAGTGG ATGTGTCAAA ACGCATACCA TTTTGAACGA TGACCTCTAA      3120

TAATTGTTAA TCATGTTGGT TACGTATTTA TTAACTTCTC CTAGTATTAG TAATTATCAT      3180

GGCTGTCATG GCGCATTAAC GGAATAAAGG GTGTGCTTAA ATCGGGCCAT TTTGCGTAAT      3240

AAGAAAAAGG ATTAATTATG AGCGAATTGA ATTAATAATA AGGTAATAGA TTTACATTAG      3300

AAAATGAAAG GGGATTTTAT GCGTGAGAAT GTTACAGTCT ATCCCTGGCG AAAGGGGGAT      3360

GTGCTGCAAG GCGATTAAGT TGGGTAACGC CAGGGTTTTC CCAGTCACGA CGTTGTAAAA      3420

CGACGGCCAG TGAGCGCGCG TAATACGACT CACTATAGGG CGAATTGGGT ACCGGGCCCC      3480

CCCTCGAGGT CGACGGTATC GATAAGCTTG ATATCGAATT CCTGCAGCCC GGGGGATCCA      3540

CTAGTTCTAG AGCGGCCGCC ACCGCGGTGG AGCTCCAGCT TTGTTCCCT TTAGTGAGGG      3600

TTAATTGCGC GCTTGGCGTA ATCATGGTCA TAGCTGTTTC CTGTGTGAAA TTGTTATCCG      3660

CTCACAATTC CACACAACAT ACGAGCCGGA AGCATAAAGT GTAAAGCCTG GGGTGCCTAA      3720

TGAGTGAGCT AACTCACATT AATTGCGTTG CGCTCACTGC CCGCTTTCCA GTCGGGAAAC      3780

CTGTCGTGCC AG                                                         3792
```

(2) INFORMATION FOR SEQ ID NO: 2:

(i) SEQUENCE CHARACTERISTICS:
        (A) LENGTH: 5234 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

```
AGGCACACGA AAAACAAGTT AAGGGATGCA GTTTATCGGG CAGCGTTGGG TCCTGGCCAC      60
GGGTGCGCAT GATCGTGCTC CTGTCGTTGA GGACCCGGCT AGGCTGGCGG GGTTGCCTTA     120
CTGGTTAGCA GAATGAATCA CCGATACGCG AGCGAACGTG AAGCGACTGC TGCTGCAAAA     180
CGTCTGCGAC CTGAGCAACA ACATGAATGG TCTTCGGTTT CCGTGTTTCG TAAAGTCTGG     240
AAACGCGGAA GTCAGCGCCC TGCACCATTA TGTTCCGGAT CTGCATCGCA GGATGCTGCT     300
GGCTACCCTG TGGAACACCT ACATCTGTAT TAACGAAGCG CTGGCATTGA CCCTGAGTGA     360
TTTTTCTCTG GTCCCGCCGC ATCCATACCG CCAGTTGTTT ACCCTCACAA CGTTCCAGTA     420
ACCGGGCATG TTCATCATCA GTAACCCGTA TCGTGAGCAT CCTCTCTCGT TTCATCGGTA     480
TCATTACCCC CATGAACAGA AATCCCCCTT ACACGGAGGC ATCAGTGACC AAACAGGAAA     540
AAACCGCCCT TAACATGGCC CGCTTTATCA GAAGCCAGAC ATTAACGCTT CTGGAGAAAC     600
TCAACGAGCT GGACGCGGAT GAACAGGCAG ACATCTGTGA ATCGCTTCAC GACCACGCTG     660
ATGAGCTTTA CCGCAGCTGC CTCGCGCGTT TCGGTGATGA CGGTGAAAAC CTCTGACACA     720
TGCAGCTCCC GGAGACGGTC ACAGCTTGTC TGTAAGCGGA TGCCGGGAGC AGACAAGCCC     780
GTCAGGGCGC GTCAGCGGGT GTTGGCGGGT GTCGGGCGC AGCCATGACC CAGTCACGTA     840
GCGATAGCGG AGTGTATACT GGCTTAACTA TGCGGCATCA GAGCAGATTG TACTGAGAGT     900
GCACCATATG CGGTGTGAAA TACCGCACAG ATGCGTAAGG AGAAAATACC GCATCAGGCG     960
CTCTTCCGCT TCCTCGCTCA CTGACTCGCT GCGCTCGGTC GTTCGGCTGC GGCGAGCGGT    1020
ATCAGCTCAC TCAAAGGCGG TAATACGGTT ATCCACAGAA TCAGGGGATA ACGCAGGAAA    1080
GAACATGTGA GCAAAAGGCC AGCAAAAGGC CAGGAACCGT AAAAAGGCCG CGTTGCTGGC    1140
GTTTTTCCAT AGGCTCCGCC CCCCTGACGA GCATCACAAA AATCGACGCT CAAGTCAGAG    1200
GTGGCGAAAC CCGACAGGAC TATAAAGATA CCAGGCGTTT CCCCCTGGAA GCTCCCTCGT    1260
GCGCTCTCCT GTTCCGACCC TGCCGCTTAC CGGATACCTG TCCGCCTTTC TCCCTTCGGG    1320
AAGCGTGGCG CTTTCTCATA GCTCACGCTG TAGGTATCTC AGTTCGGTGT AGGTCGTTCG    1380
CTCCAAGCTG GGCTGTGTGC ACGAACCCCC CGTTCAGCCC GACCGCTGCG CCTTATCCGG    1440
TAACTATCGT CTTGAGTCCA ACCCGGTAAG ACACGACTTA TCGCCACTGG CAGCAGTCCC    1500
TTAACTTACT TATTAAATAA TTTATAGCTA TTGAAAAGAG ATAAGAATTG TTCAAAGCTA    1560
ATATTGTTTA AATCGTCAAT TCCTGCATGT TTTAAGGAAT TGTTAAATTG ATTTTTTGTA    1620
AATATTTTCT TGTATTCTTT GTTAACCCAT TTCATAACGA ATAATTATA CTTTTGTTTA     1680
TCTTTGTGTG ATATTCTTGA TTTTTTTCTA CTTAATCTGA TAAGTGAGCT ATTCACTTTA    1740
GGTTTAGGAT GAAAATATTC TCTTGGAACC ATACTTAATA TAGAAATATC AACTTCTGCC    1800
ATTAAAGTA ATGCCAATGA GCGTTTTGTA TTTAATAATC TTTTAGCAAA CCCGTATTCC     1860
ACGATTAAAT AAATCTCATT AGCTATACTA TCAAAAACAA TTTTGCGTAT TATATCCGTA    1920
CTTATGTTAT AAGGTATATT ACCATATATT TTATAGGATT GGTTTTTAGG AAATTTAAAC    1980
TGCAATATAT CCTTGTTTAA AACTTGGAAA TTATCGTGAT CAACAAGTTT ATTTTCTGTA    2040
```

```
GTTTTGCATA ATTTATGGTC TATTTCAATG GCAGTTACGA AATTACACCT CTTTACTAAT    2100

TCAAGGGTAA AATGGCCTTT TCCTGAGCCG ATTTCAAAGA TATTATCATG TTCATTTAAT    2160

CTTATATTTG TCATTATTTT ATCTATATTA TGTTTTGAAG TAATAAAGTT TTGACTGTGT    2220

TTTATATTTT TCTCGTTCAT TATAACCCTC TTTAATTTGG TTATATGAAT TTTGCTTATT    2280

AACGATTCAT TATAACCACT TATTTTTTGT TTGGTTGATA ATGAACTGTG CTGATTACAA    2340

AAATACTAAA AATGCCCATA TTTTTTCCTC CTTATAAAAT TAGTATAATT ATAGCACGAG    2400

CTCTGATAAA TATGAACATG ATGAGTGATC GTTAAATTTA TACTGCAATC GGATGCGATT    2460

ATTGAATAAA AGATATGAGA GATTTATCTA ATTTCTTTTT TCTTGTAAAA AAAGAAAGTT    2520

CTTAAAGGTT TTATAGTTTT GGTCGTAGAG CACACGGTTT AACGACTTAA TTACGAAGTA    2580

AATAAGTCTA GTGTGTTAGA CTTTATGAAA TCTATATACG TTTATATATA TTTATTATCC    2640

GATTTTTTAT TAAAACGTCT CAAAATCGTT TCTGAGACGT TTTAGCGTTT ATTTCGTTTA    2700

GTTATCGGCA TAATCGTTAA AACAGGCGTT ATCGTAGCGT AAAAGCCCTT GAGCGTAGCG    2760

TGGCTTTGCA GCGAAGATGT TGTCTGTTAG ATTATGAAAG CCGATGACTG AATGAAATAA    2820

TAAGCGCAGC GCCCTTCTAT TTCGGTTGGA GGAGGCTCAA GGGAGTATGA GGGAATGAAA    2880

TTCCCTCATG GGTTTGATTT TAAAAATTGC TTGCAATTTT GCCGAGCGGT AGCGCTGGAA    2940

AATTTTTGAA AAAAATTTGG AATTTGGAAA AAAATGGGGG GAAAGGAAGC GAATTTTGCT    3000

TCCGTACTAC GACCCCCCAT TAAGTGCCGA GTGCCAATTT TTGTGCCAAA AACGCTCTAT    3060

CCCAACTGGC TCAAGGGTTT AAGGGGTTTT TCAATCGCCA ACGAATCGCC AACGTTTTCG    3120

CCAACGTTTT TTATAAATCT ATATTTAAGT AGCTTTATTG TTGTTTTTAT GATTACAAAG    3180

TGATACACTA ACTTTATAAA ATTATTTGAT TGGAGTTTTT TAAATGGTGA TTTCAGAATC    3240

GAAAAAAAGA GTTATGATTT CTCTGACAAA AGAGCAAGAT AAAAAATTAA CAGATATGGC    3300

GAAACAAAAA GGTTTTTCAA AATCTGCGGT TGCGGCGTTA GCTATAGAAG AATATGCAAG    3360

AAAGGAATCA GAACAAAAAA AATAAGCGAA AGCTCGCGTT TTTAGAAGGA TACGAGTTTT    3420

CGCTACTTGT TTTTGATAAG GTAATTATAT CATGGCTATT AAAAATACTA AAGCTAGAAA    3480

TTTTGGATTT TTATTATATC CTGACTCAAT TCCTAATGAT TGGAAAGAAA AATTAGAGAG    3540

TTTGGGCGTA TCTATGGCTG TCAGTCCTTT ACACGATATG GACGAAAAAA AAGATAAAGA    3600

TACATGGAAT AATAGTAATA TTATACAAAA TGGAAAGCAC TATAAAAAAC CACACTATCA    3660

CGTTATATAT ATTGCACGAA ATCCTGTAAC AATAGAAAGC GTTAGGAACA AGATTAAGCG    3720

AAAATTGGGG AATAGTTCAG TTGCTCATGT TGAGATACTT GATTATATCA AAGGTTCATA    3780

TGAATATTTG ACTCATGAAT CAAAGGACGC TATTGCTAAG AATAAACATA TATACGACAA    3840

AAAAGATATT TTGAACATTA ATGATTTTGA TATTGACCGC TATATAACAC TTGATGAAAG    3900

CCAAAAAAGA GAATTGAAGA ATTTACTTTT AGATATAGTG GATGACTATA ATTTGGTAAA    3960

TACAAAAGAT TTAATGGCTT TTATTCGCCT TAGGGGAGCG GAGTTTGGAA TTTTAAATAC    4020

GAATGATGTA AAAGATATTG TTTCAACAAA CTCTAGCGCC TTTAGATTAT GGTTTGAGGG    4080

CAATTATCAG TGTGGATATA GAGCAAGTTA TGCAAAGGTT CTTGATGCTG AAACGGGGGA    4140

AATAAAATGA CAAACAAAGA AAAAGAGTTA TTTGCTGAAA ATGAGGAATT AAAAAAAGAA    4200

ATTAAGGACT TAAAAGAGCG TATTGAAAGA TACAGAGAAA TGGAAGTTGA ATTAAGTACA    4260

ACAATAGATT TATTGAGAGG AGGGATTATT GAATAAATAA AAGCCCCCTG ACGAAAGTCG    4320

AAGGGGGTTT TTATTTTGGT TTGATGTTGC GATTAATAGC AATACAATTG CAATAAACAA    4380
```

```
AATGATCTTC CTTCAGGTTA TGACCATCTG TGCCAGTTCG TAATGTCTGG TCAACTTTCC    4440

GACTCTGAGA AACTTCTGGA ATCGCTAGAG AATTTCTGGA ATGGGATTCA GGAGTGGACA    4500

GAACGACACG GATATATAGT GGATGTGTCA AAACGCATAC CATTTTGAAC GATGACCTCT    4560

AATAATTGTT AATCATGTTG GTTACGTATT TATTAACTTC TCCTAGTATT AGTAATTATC    4620

ATGGCTGTCA TGGCGCATTA ACGGAATAAA GGGTGTGCTT AAATCGGGCC ATTTTGCGTA    4680

ATAAGAAAAA GGATTAATTA TGAGCGAATT GAATTAATAA TAAGGTAATA GATTTACATT    4740

AGAAAATGAA AGGGGATTTT ATGCGTGAGA ATGTTACAGT CTATCCCTGG CGAAAGGGGG    4800

ATGTGCTGCA AGGCGATTAA GTTGGGTAAC GCCAGGGTTT TCCCAGTCAC GACGTTGTAA    4860

AACGACGGCC AGTGAGCGCG CGTAATACGA CTCACTATAG GGCGAATTGG GTACCGGGCC    4920

CCCCCTCGAG GTCGACGGTA TCGATAAGCT TGATATCGAA TTCCTGCAGC CCGGGGGATC    4980

CACTAGTTCT AGAGCGGCCG CCACCGCGGT GGAGCTCCAG CTTTTGTTCC CTTTAGTGAG    5040

GGTTAATTGC GCGCTTGGCG TAATCATGGT CATAGCTGTT TCCTGTGTGA AATTGTTATC    5100

CGCTCACAAT TCCACACAAC ATACGAGCCG GAAGCATAAA GTGTAAAGCC TGGGGTGCCT    5160

AATGAGTGAG CTAACTCACA TTAATTGCGT TGCGCTCACT GCCCGCTTTC CAGTCGGGAA    5220

ACCTGTCGTG CCAG                                                     5234

(2) INFORMATION FOR SEQ ID NO: 3:

(i) SEQUENCE CHARACTERISTICS:
        (A) LENGTH: 6722 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

CGATTCACAA AAAATAGGCA CACGAAAAAC AAGTTAAGGG ATGCAGTTTA AATTCTTGAA      60

GACGAAAGGG CCTCGTGATA CGCCTATTTT TATAGGTTAA TGTCATGATA ATAATGGTTT     120

CTTAGACGTC AGGTGGCACT TTTCGGGGAA ATGTGCGCGG AACCCCTATT TGTTTATTTT     180

TCTAAATACA TTCAAATATG TATCCGCTCA TGAGACAATA ACCCTGATAA ATGCTTCAAT     240

AATATTGAAA AAGGAAGAGT ATGAGTATTC AACATTTCCG TGTCGCCCTT ATTCCCTTTT     300

TTGCGGCATT TGCCTTCCT GTTTTTGCTC ACCCAGAAAC GCTGGTGAAA GTAAAAGATG      360

CTGAAGATCA GTTGGGTGCA CGAGTGGGTT ACATCGAACT GGATCTCAAC AGCGGTAAGA     420

TCCTTGAGAG TTTTCGCCCC GAAGAACGTT TTCCAATGAT GAGCACTTTT AAAGTTCTGC     480

TATGTGGCGC GGTATTATCC CGTGTTGACG CCGGGCAAGA GCAACTCGGT CGCCGCATAC     540

ACTATTCTCA GAATGACTTG GTTGAGTACT CACCAGTCAC AGAAAAGCAT CTTACGGATG     600

GCATGACAGT AAGAGAATTA TGCAGTGCTG CCATAACCAT GAGTGATAAC ACTGCGGCCA     660

ACTTACTTCT GACAACGATC GGAGGACCGA AGGAGCTAAC CGCTTTTTTG CACAACATGG     720

GGGATCATGT AACTCGCCTT GATCGTTGGG AACCGGAGCT GAATGAAGCC ATACCAAACG     780

ACGAGCGTGA CACCACGATG CCTGCAGCAA TGGCAACAAC GTTGCGCAAA CTATTAACTG     840

GCGAACTACT TACTCTAGCT TCCCGGCAAC AATTAATAGA CTGGATGGAG GCGGATAAAG     900

TTGCAGGACC ACTTCTGCGC TCGGCCCTTC CGGCTGGCTG GTTTATTGCT GATAAATCTG     960

GAGCCGGTGA GCGTGGGTCT CGCGGTATCA TTGCAGCACT GGGGCCAGAT GGTAAGCCCT    1020

CCCGTATCGT AGTTATCTAC ACGACGGGGA GTCAGGCAAC TATGGATGAA CGAAATAGAC    1080
```

-continued

```
AGATCGCTGA GATAGGTGCC TCACTGATTA AGCATTGGTA ACTGTCAGAC CAAGTTTACT    1140

CATATATACT TTAGATTGAT TTAAAACTTC ATTTTTAATT TAAAAGGATC TAGGTGAAGA    1200

TCCTTTTTGA TAATCTCATG ACCAAAATCC CTTAACGTGA GTTTTCGTTC CACTGAGCGT    1260

CAGACCCCGT AGAAAAGATC AAAGGATCTT CTTGAGATCC TTTTTTTCTG CGCGTAATCT    1320

GCTGCTTGCA AACAAAAAAA CCACCGCTAC CAGCGGTGGT TTGTTTGCCG GATCAAGAGC    1380

TACCAACTCT TTTTCCGAAG GTAACTGGCT TCAGCAGAGC GCAGATACCA AATACTGTCC    1440

TTCTAGTGTA GCCGTAGTTA GGCCACCACT TCAAGAACTC TGTAGCACCG CCTACATACC    1500

TCGCTCTGCT AATCCTGTTA CCAGTGGCTG CTGCCAGTGG CGATAAGTCG TGTCTTACCG    1560

GGTTGGACTC AAGACGATAG TTACCGGATA AGGCGCAGCG GTCGGGCTGA ACGGGGGGTT    1620

CGTGCACACA GCCCAGCTTG GAGCGAACGA CCTACACCGA ACTGAGATAC CTACAGCGTG    1680

AGCTATGAGA AAGCGCCACG CTTCCCGAAG GGAGAAAGGC GGACAGGTAT CCGGTAAGCG    1740

GCAGGGTCGG AACAGGAGAG CGCACGAGGG AGCTTCCAGG GGGAAACGCC TGGTATCTTT    1800

ATAGTCCTGT CGGGTTTCGC CACCTCTGAC TTGAGCGTCG ATTTTTGTGA TGCTCGTCAG    1860

GGGGGCGGAG CCTATGGAAA AACGCCAGCA ACGCGGCCTT TTTACGGTTC CTGGCCTTTT    1920

GCTGGCCTTT TGCTCACATG TTCTTTCCTG CGTTATCCCC TGATTCTGTG ATAACCGTA    1980

TTACCGCCTT TGAGTGAGCT GATACCGCTC GCCGCAGCCG AACGACCGAG CGCAGCGAGT    2040

CAGTGAGCGA GGAAGCGGAA GAGCGCCTGA TGCGGTATTT TCTCCTTACG CATCTGTGCG    2100

GTATTTCACA CCGCATATGG TGCACTCTCA GTACAATCTG CTCTGATGCC GCATAGTTAA    2160

GCCAGTATAC ACTCCGCTAT CGCTACGTGA CTGGGTCATG GCTGCGCCCC GACACCCGCC    2220

AACACCCGCT GACGCGCCCT GACGGGCTTG TCTGCTCCCG GCATCCGCTT ACAGACAAGC    2280

TGTGACCGTC TCCGGGAGCT GCATGTGTCA GAGGTTTTCA CCGTCATCAC CGAAACGCGC    2340

GAGGCAGCTG CGGTAAAGCT CATCAGCGTG GTCGTGAAGC GATTCACAGA TGTCTGCCTG    2400

TTCATCCGCG TCCAGCTCGT TGAGTTTCTC CAGAAGCGTT AATGTCTGGC TTCTGATAAA    2460

GCGGGCCATG TTAAGGGCGG TTTTTTCCTG TTTGGTCACT GATGCCTCCG TGTAAGGGGG    2520

ATTTCTGTTC ATGGGGGTAA TGATACCGAT GAAACGAGAG AGGATGCTCA CGATACGGGT    2580

TACTGATGAT GAACATGCCC GGTTACTGGA ACGTTGTGAG GGTAAACAAC TGGCGGTATG    2640

GATGCGGCGG GACCAGAGAA AAATCACTCA GGGTCAATGC CAGCGCTTCG TTAATACAGA    2700

TGTAGGTGTT CCACAGGGTA GCCAGCAGCA TCCTGCGATG CAGATCCGGA ACATAATGGT    2760

GCAGGGCGCT GACTTCCGCG TTTCCAGACT TTACGAAACA CGGAAACCGA AGACCATTCA    2820

TGTTGTTGCT CAGGTCGCAG ACGTTTTGCA GCAGCAGTCG CTTCACGTTC GCTCGCGTAT    2880

CGGTGATTCA TTCTGCTAAC CAGTAAGGCA ACCCCGCCAG CCTAGCCGGG TCCTCAACGA    2940

CAGGAGCACG ATCATGCGCA CCCGTGGCCA GGACCCAACG CTGCTCCCTT AACTTACTTA    3000

TTAAATAATT TATAGCTATT GAAAAGAGAT AAGAATTGTT CAAAGCTAAT ATTGTTTAAA    3060

TCGTCAATTC CTGCATGTTT TAAGGAATTG TTAAATTGAT TTTTTGTAAA TATTTTCTTG    3120

TATTCTTTGT TAACCCATTT CATAACGAAA TAATTATACT TTTGTTTATC TTTGTGTGAT    3180

ATTCTTGATT TTTTCTACT TAATCTGATA AGTGAGCTAT TCACTTTAGG TTAGGATGA    3240

AAATATTCTC TTGGAACCAT ACTTAATATA GAAATATCAA CTTCTGCCAT TAAAAGTAAT    3300

GCCAATGAGC GTTTTGTATT TAATAATCTT TTAGCAAACC CGTATTCCAC GATTAAATAA    3360

ATCTCATTAG CTATACTATC AAAAACAATT TTGCGTATTA TATCCGTACT TATGTTATAA    3420

GGTATATTAC CATATATTTT ATAGGATTGG TTTTTAGGAA ATTTAAACTG CAATATATCC    3480
```

```
TTGTTTAAAA CTTGGAAATT ATCGTGATCA ACAAGTTTAT TTTCTGTAGT TTTGCATAAT    3540

TTATGGTCTA TTTCAATGGC AGTTACGAAA TTACACCTCT TTACTAATTC AAGGGTAAAA    3600

TGGCCTTTTC CTGAGCCGAT TTCAAAGATA TTATCATGTT CATTTAATCT TATATTTGTC    3660

ATTATTTTAT CTATATTATG TTTTGAAGTA ATAAAGTTTT GACTGTGTTT TATATTTTTC    3720

TCGTTCATTA TAACCCTCTT TAATTTGGTT ATATGAATTT TGCTTATTAA CGATTCATTA    3780

TAACCACTTA TTTTTTGTTT GGTTGATAAT GAACTGTGCT GATTACAAAA ATACTAAAAA    3840

TGCCCATATT TTTTCCTCCT TATAAAATTA GTATAATTAT AGCACGAGCT CTGATAAATA    3900

TGAACATGAT GAGTGATCGT TAAATTTATA CTGCAATCGG ATGCGATTAT TGAATAAAAG    3960

ATATGAGAGA TTTATCTAAT TTCTTTTTTC TTGTAAAAAA AGAAAGTTCT TAAAGGTTTT    4020

ATAGTTTTGG TCGTAGAGCA CACGGTTTAA CGACTTAATT ACGAAGTAAA TAAGTCTAGT    4080

GTGTTAGACT TTATGAAATC TATATACGTT TATATATATT TATTATCCGA TTTTTTATTA    4140

AAACGTCTCA AAATCGTTTC TGAGACGTTT TAGCGTTTAT TTCGTTTAGT TATCGGCATA    4200

ATCGTTAAAA CAGGCGTTAT CGTAGCGTAA AAGCCCTTGA GCGTAGCGTG GCTTTGCAGC    4260

GAAGATGTTG TCTGTTAGAT TATGAAAGCC GATGACTGAA TGAAATAATA AGCGCAGCGC    4320

CCTTCTATTT CGGTTGGAGG AGGCTCAAGG GAGTATGAGG GAATGAAATT CCCTCATGGG    4380

TTTGATTTTA AAAATTGCTT GCAATTTTGC CGAGCGGTAG CGCTGGAAAA TTTTTGAAAA    4440

AAATTTGGAA TTTGGAAAAA AATGGGGGGA AAGGAAGCGA ATTTTGCTTC CGTACTACGA    4500

CCCCCCCATTA AGTGCCGAGT GCCAATTTTT GTGCCAAAAA CGCTCTATCC CAACTGGCTC    4560

AAGGGTTTAA GGGGTTTTTC AATCGCCAAC GAATCGCCAA CGTTTTCGCC AACGTTTTTT    4620

ATAAATCTAT ATTTAAGTAG CTTTATTGTT GTTTTTATGA TTACAAAGTG ATACACTAAC    4680

TTTATAAAAT TATTTGATTG GAGTTTTTTA AATGGTGATT TCAGAATCGA AAAAAAGAGT    4740

TATGATTTCT CTGACAAAAG AGCAAGATAA AAAATTAACA GATATGGCGA AACAAAAAGG    4800

TTTTTCAAAA TCTGCGGTTG CGGCGTTAGC TATAGAAGAA TATGCAAGAA AGGAATCAGA    4860

ACAAAAAAAA TAAGCGAAAG CTCGCGTTTT TAGAAGGATA CGAGTTTTCG CTACTTGTTT    4920

TTGATAAGGT AATTATATCA TGGCTATTAA AAATACTAAA GCTAGAAATT TTGGATTTTT    4980

ATTATATCCT GACTCAATTC CTAATGATTG GAAAGAAAAA TTAGAGAGTT TGGGCGTATC    5040

TATGGCTGTC AGTCCTTTAC ACGATATGGA CGAAAAAAAA GATAAAGATA CATGGAATAA    5100

TAGTAATATT ATACAAAATG GAAAGCACTA TAAAAAACCA CACTATCACG TTATATATAT    5160

TGCACGAAAT CCTGTAACAA TAGAAAGCGT TAGGAACAAG ATTAAGCGAA AATTGGGGAA    5220

TAGTTCAGTT GCTCATGTTG AGATACTTGA TTATATCAAA GGTTCATATG AATATTTGAC    5280

TCATGAATCA AAGGACGCTA TTGCTAAGAA TAAACATATA TACGACAAAA AAGATATTTT    5340

GAACATTAAT GATTTTGATA TTGACCGCTA TATAACACTT GATGAAAGCC AAAAAAGAGA    5400

ATTGAAGAAT TTACTTTTAG ATATAGTGGA TGACTATAAT TTGGTAAATA CAAAAGATTT    5460

AATGGCTTTT ATTCGCCTTA GGGGAGCGGA GTTTGGAATT TTAAATACGA ATGATGTAAA    5520

AGATATTGTT TCAACAAACT CTAGCGCCTT TAGATTATGG TTTGAGGGCA ATTATCAGTG    5580

TGGATATAGA GCAAGTTATG CAAAGGTTCT TGATGCTGAA ACGGGGGAAA TAAAATGACA    5640

AACAAAGAAA AAGAGTTATT TGCTGAAAAT GAGGAATTAA AAAAAGAAAT TAAGGACTTA    5700

AAAGAGCGTA TTGAAAGATA CAGAGAAATG GAAGTTAATA AAGTACAAC AATAGATTTA    5760

TTGAGAGGAG GGATTATTGA ATAAATAAAA GCCCCCTGAC GAAAGTCGAA GGGGGTTTTT    5820
```

-continued

```
ATTTTGGTTT GATGTTGCGA TTAATAGCAA TACAATTGCA ATAAACAAAA TGATCTTCCT    5880

TCAGGTTATG ACCATCTGTG CCAGTTCGTA ATGTCTGGTC AACTTTCCGA CTCTGAGAAA    5940

CTTCTGGAAT CGCTAGAGAA TTTCTGGAAT GGGATTCAGG AGTGGACAGA ACGACACGGA    6000

TATATAGTGG ATGTGTCAAA ACGCATACCA TTTTGAACGA TGACCTCTAA TAATTGTTAA    6060

TCATGTTGGT TACGTATTTA TTAACTTCTC CTAGTATTAG TAATTATCAT GGCTGTCATG    6120

GCGCATTAAC GGAATAAAGG GTGTGCTTAA ATCGGGCCAT TTTGCGTAAT AAGAAAAAGG    6180

ATTAATTATG AGCGAATTGA ATTAATAATA AGGTAATAGA TTTACATTAG AAAATGAAAG    6240

GGGATTTTAT GCGTGAGAAT GTTACAGTCT ATCCCTGGCG AAAGGGGGAT GTGCTGCAAG    6300

GCGATTAAGT TGGGTAACGC CAGGGTTTTC CCAGTCACGA CGTTGTAAAA CGACGGCCAG    6360

TGAGCGCGCG TAATACGACT CACTATAGGG CGAATTGGGT ACCGGGCCCC CCCTCGAGGT    6420

CGACGGTATC GATAAGCTTG ATATCGAATT CCTGCAGCCC GGGGGATCCA CTAGTTCTAG    6480

AGCGGCCGCC ACCGCGGTGG AGCTCCAGCT TTTGTTCCCT TTAGTGAGGG TTAATTGCGC    6540

GCTTGGCGTA ATCATGGTCA TAGCTGTTTC CTGTGTGAAA TTGTTATCCG CTCACAATTC    6600

CACACAACAT ACGAGCCGGA AGCATAAAGT GTAAAGCCTG GGGTGCCTAA TGAGTGAGCT    6660

AACTCACATT AATTGCGTTG CGCTCACTGC CCGCTTTCCA GTCGGGAAAC CTGTCGTGCC    6720

AG                                                                 6722
```

TEMPERATURE-SENSITIVE PLASMID

FIELD OF THE INVENTION

The present invention relates to a plasmid which is usable for the genetic modification of bacteria displaying positive Gram staining, especially lactic bacteria of industrial or medical importance.

It also relates to bacteria containing such a plasmid. Lastly, it relates to genetic modification methods employing such a plasmid, either to inactivate a gene normally present in the bacterial chromosome, or to introduce and express a gene of interest.

BACKGROUND OF THE INVENTION

Many Gram bacteria displaying positive Gram staining are subjects of study as a biological model (for example bacteria of the genus Bacillus), as a fermentation strain of industrial importance (lactic acid bacteria) or as a pathogen (for example Clostridia, Listeria, Staphylococcus, Streptococcus). Many of these strains are characterized from a physiological standpoint, but few have been studied or modified genetically. The study or modification of the strains may be facilitated by the use of vectors permitting directed or non-specific insertions into the bacterial chromosome. Delivery systems which are based on the non-replicative vectors are limited to bacteria which can be transformed with a high frequency, and those utilizing replicons which are active only under certain conditions are often limited to their host range. Thus, the construction of recombinant strains requires considerable effort, and can be applied efficaciously only to certain specific micro-organisms.

The addition, loss or modification of genes can transform the role of an organism in an industrial process such as fermentation.

Biotechnology seeks to facilitate the industrial use of microorganisms. For example, lactic bacteria are used in agri-foodstuffs, predominantly for the manufacture of fermented dairy products, but also outside the milk industry for the manufacture of wine, cider, cooked meats and silage.

It is hence especially desirable to have effective means available for introducing or modifying specifically and permanently certain genes in these organisms.

At the present time, modification of the chromosome in lactic bacteria is performed via a system by transformation of a non-replicative plasmid. In a single step, it is necessary to have two low-frequency events, transformation with a plasmid and recombination in the chromosome. The probability of obtaining these two events in a single step is the product of the probabilities of each; there is hence a very small chance of obtaining the modification.

Plasmid pWV01 is a cryptic plasmid initially isolated in *Lactococcus lactis* subsp. *cremoris;* it is a broad-host-range plasmid which is replicative in both Gram-positive and Gram-negative bacteria, in particular in *E. coli, Bacillus subtilis, Lactococcus lactis* Streptococcus and Lactobacillus. It has been characterized, and its nucleotide sequence has been published by Leenhouts et al. (1991).

In Application WO 85/03495, large fragments of this plasmid are used to construct a recombinant plasmid pGK12 marked with the gene for resistance to erythromycin and/or the gene for resistance to chloramphenicol (chloramphenicol acetyltransferase (CAT)). This plasmid pGK12 cannot be used to make integrations in the bacterial chromosome.

The non-replicative plasmids used hitherto enable this problem to be alleviated, but this system requires high degrees of transformation to permit the detection of low-frequency events such as transposition or recombination in the chromosome; now, most lactic bacteria are weakly transformable.

It would be possible to overcome all these difficulties by obtaining a temperature-sensitive replicon which could be used as a delivery vector in lactic or other bacteria.

Plasmids pE194 and pSH71 have been described as naturally temperature-sensitive, above a temperature of 51° C. (J. Bacteriol., 1990, 172, 4543–4548).

SUMMARY OF THE INVENTION

Thus, the subject of the present invention is a bacterial vector plasmid of the type containing an origin of replication which is effective in Gram+ bacteria, characterized in that it contains at least:

a marker gene which is expressed in a bacterial host strain,
an effective replication system which is temperature-sensitive (Ts) at and above a temperature compatible with the viability of the host strain,
and in that the temperature of inhibition of replication is below or equal to approximately 37° C.

The fact that the plasmid according to the invention is non-replicative at 37° C. makes it especially suitable in the case where the bacteria have a relatively low growth temperature, or when a substantial thermal shock is not desirable. The plasmid according to the invention can be used alone, it does not have to be combined with another plasmid. The inhibition of replication by temperatures above approximately 37° C. is not strain-dependent. It possesses a broad host range and can establish itself, in particular, in the traditional strains belonging to the group comprising: Bacillus, Enterococcus, Lactobacillus, Lactococcus, Streptococcus, Listeria, Pediococcus, Staphylococcus, Clostridia, Leuconostoc, *E. coli, B. subtilis, E. faecalis, L. fermentum, L. helveticus, L. bulgaricus, L. lactis, S. pyogenes, S. thermophilus, S. sanguis, L. Monocytogenes.*

The plasmid according to the invention carries at least one gene coding for a selectable marker, as well as the elements needed for its expression, such as promoter, ribosome binding site, terminator, and the like. Selectable genes are, for example, genes for resistance to antibiotics (erythromycin, chloramphenicol), or genes permitting growth on a medium lacking certain ingredients, and the like.

The marker gene is integrated in the chromosome in the case of recombination.

Replication system is understood to mean a system comprising an origin of replication as well as the protein which induces its functioning; said protein is inactivated above a temperature which inhibits the replication system.

Such a plasmid replicates normally at 28° C. in a large number of bacteria. At a temperature above approximately 35° C., the replication of this plasmid is inhibited; this temperature which inhibits replication of the plasmid is relatively low, and permits multiplication and normal growth of most bacteria, especially lactic bacteria. The temperature recommended for the effective inactivation of this plasmid is 37° C.

According to one of its aspects, the subject of the present invention is a vector plasmid, characterized in that it contains the larger Cla I; fragment of plasmid pWV01, possessing at least one mutation in the ThaI I-Rsa I region.

More especially, a vector plasmid displaying temperature-sensitive replication according to the invention possesses at least one mutation in the region corresponding to RepA of plasmid pWV01. The RepA protein is encoded by one of the 4 open reading frames (ORF) identified on pWV01, ORF A, and is necessary for replication.

Preferred mutations of this plasmid are located in positions 972, 977, 980 and 987 of the nucleotide sequence of pWV01.

The RepA protein encoded by the plasmid according to the invention possesses, relative to the wild-type, the modifications shown in FIG. 3, namely the replacement of:
Ser by Asn,
Asp by Asn,
Val by Ile,
Arg by Gln.

Such a plasmid constitutes a broad-host-range suicide vector of a type which is unique up to the present in the field of lactic bacteria.

In effect, it enables integration in the chromosome to be split into two steps. In the first, transformation step, the plasmid is established in the cell. In the second step, the event of integration in the chromosome is selected by raising the temperature. Bacteria which are supposedly difficult to transform may thus be modified genetically.

More especially, plasmids according to the invention contain one of the sequences shown in one of FIGS. 9, 10 and 11, or a sequence representing at least 80% homology with these sequences.

The genetic tools thus developed enable genes to be introduced into the bacterial chromosome and stabilized therein.

The application of a method employing homologous recombination is, for example, chosen.

To this end, a temperature-sensitive replicon according to the invention, which contains, in addition, at least one DNA fragment homologous with the chromosomal DNA of the bacterium which it is desired to modify, is used.

According to one of its aspects, the subject of the present invention is a method for the inactivation of a gene present in the chromosome of a bacterium, characterized in that:
a) the plasmid according to the invention is introduced into the bacterium by transformation,
b) the bacterium is cultured on selective medium at a temperature below the temperature of inhibition of the origin of replication,
c) the culture temperature is raised to a temperature above said temperature of inhibition,
d) the surviving bacteria are recovered after several multiplication cycles, at a temperature of inhibition of plasmid replication.

Step d) enables the bacteria carrying the plasmid marker to be selected.

The chromosomal fragment cloned into the plasmid can correspond to a precise gene, which is specifically inactivated by integration of the plasmid in the chromosomal copy of the gene. In the bacterial population, only this integration site will be found.

In another embodiment, the bacterial DNA present in the plasmid may be chosen from a library of chromosomal fragments for cloning, and there will be integration at random; the integration site of the plasmid differs from one bacterium to another, and mutagenesis is thus produced.

The method may also be applied to a temperature-sensitive replicon carrying a transposon. Different transposons are available for mutagenizing the chromosome.

The Ts plasmid is employed as a carrier of one of these transposons, and is, where appropriate, modified so as to be active in *L. lactis*. Each transposon carries a marker gene (e.g.: resistance gene). By applying the protocol described above (a to c), cells which have integrated the transposon in their chromosomes are obtained. These cells are selected by means of the transposon marker. In the case of transposition, the plasmid is not integrated in the chromosome.

As a variant, the vector plasmid according to the invention also contains a mobilization locus permitting conjugation. Preferably, this mobilization locus is the ori T locus, extracted from a plasmid of a Gram-positive bacterium, and which can preferably be extracted from a Streptococcus plasmid. The vector plasmid carrying this locus can be mobilized and transferred by conjugation into non-transformable bacterial species.

The method for the inactivation of a gene in a bacterium then involves the following steps:
a) a plasmid according to the invention, carrying a mobilization locus and a fragment homologous with the chromosome and/or a transposon, is introduced into the bacterium by conjugation,
b) the bacterium is cultured on selective medium at a temperature below the temperature of inhibition of the origin of replication,
c) the culture temperature is raised to a temperature above said temperature of inhibition,
d) the surviving bacteria are recovered after several multiplication cycles, at a temperature of inhibition of plasmid replication.

The bacteria obtained at the end of step d) have undergone a recombination or transposition event and carry the marker of the transposon or of the plasmid.

As a variant, the vector plasmid according to the invention also contains a replicon which is active in *E. coli*. The vector plasmid carrying this locus, and these [sic] derivatives, may be propagated in *E. Coli* [sic] The constructions prepared and propagated in *E. coli* at 37° C. (by means of the second replicon) may then be transferred to lactic bacteria in which only the Ts replicon will be active.

In the methods described above, after introduction of the vector plasmid into the bacterium by transformation or conjugation in step a), the plasmid is allowed to establish itself in the bacterial population, by replication, at 28–30° C.

The selectable character is expressed in all the bacteria. When the temperature rises above 35° C., the plasmid in free form becomes incapable of replicating and is hence lost during the cell divisions. Only the bacteria for which this plasmid has become integrated by recombination in the chromosome, or for which the transposon has become integrated in the chromosome, retain and transmit the genetic information carried by the plasmid or the transposon, and enabling them to grow on selective medium. The low-frequency integration events are thus selected by recovering the bacteria which multiply at 35–37° C. on selective medium.

When the plasmid is integrated in the chromosome, it possesses excellent stability, which can be of the order of 99% after 75 generations at 37.5° C.

The scheme followed for integration of the plasmid by homologous recombination is illustrated in FIG. 6.

*L. lactis* strain VE 6002, containing plasmid pVE6002 according to the invention, was deposited on Mar. 11, 1992 with the national collection of the Pasteur Institute, 25–28 rue du Docteur Roux, Paris, under number I-1179. All restrictions imposed on the availability of the deposited biological material will be irrevocably removed upon the granting of the patent.

According to another of its aspects, the subject of the invention is a method enabling a heterologous gene to be introduced into a bacterium. For its implementation, a temperature-sensitive vector plasmid as has been able to be defined above, and containing, in addition, a gene coding for a protein of interest, is used under the control of the elements needed for its expression, and which are known to a person skilled in the art. Where appropriate, this gene may be carried by the transposon. The steps described below are then followed.

a) a plasmid according to the invention is introduced into the bacterium by transformation or conjugation,
b) the bacterium is cultured on selective medium at a temperature below the temperature of inhibition of the origin of replication,
c) the culture temperature is raised to a temperature above said temperature of inhibition,
d) the surviving bacteria are recovered after several multiplication cycles, at a temperature of inhibition of plasmid replication.

Step d) enables the bacteria carrying the marker of the plasmid or of the transposon to be selected.

The subject of the invention is also bacteria containing a plasmid according to the invention, in free form or integrated in the chromosome.

Such bacteria will find, in particular, applications in the field of the agri-foodstuffs, especially the dairy or cheese-making, industry.

In some of the cases described above, it is desired to be able to remove all or part of the genetic material introduced into the bacterial chromosome by the method according to the invention.

The homologous recombination method permits two steps: the first consists in selecting the event of integration of the plasmid, the second step—which is optional—consists in excising from the chromosome the replicon and the markers which do not correspond to food standards.

Excision of the replicon: integration by homologous recombination creates duplications on both sides of the Ts plasmid (FIG. 7a). It has been shown that a replicative rolling-circle plasmid integrated in the chromosome strongly stimulates homologous recombination between the neighboring sequences. When the chromosomal fragment carried by the Ts plasmid contains a marker, the duplications created by the integration enable the replicon to be excised, leaving an inactive chromosomal gene (FIG. 7a). Experimentally, the procedure entails culturing at 28° C. the strain containing the integrated plasmid (selected previously at 37° C.). At a permissive temperature, replication resumes and stimulates recombination between the repeat sequences, leading to deletion of the replicon (FIG. 7a).

The subject of the present invention is also a vector plasmid displaying temperature-sensitive replication, possessing one or more of the features already described, and in which an internal region is duplicated. The two identical sequences are placed in such a way as to flank the region which it is desired to remove. Such a plasmid is then used in a method for the inactivation of a gene or for the introduction of a heterologous gene by recombination in the bacterial chromosome, as are described above.

At the end of step d), the surviving bacteria are cultured again at a temperature below the temperature of inhibition, for example at 28–30° C., on non-selective medium. In effect, a replicative plasmid strongly stimulates homologous recombination between the neighboring sequences. The strain containing the integrated plasmid and selected previously at 35–37° C. is cultured at a permissive temperature: plasmid replication resumes, stimulating recombination between the repeat sequences. The replicon and the markers which are incompatible with, for example, a use of this system in agri-foodstuffs are excised, with possible retention of the modified gene. Selection of the bacteria which have excised the undesirable markers is done after plating out at a non-permissive temperature. This mechanism is illustrated in FIG. 7b.

BRIEF DESCRIPTION OF THE DRAWINGS

Reference will be made to the following figures:

FIGS. 1A–1 through 1B–2: Kinetics of loss and analysis of the copy number of pVE6002 according to the invention and of non-Ts pVE6001. L. lactis subsp. lactis IL 1403 carrying plasmid pGK12, pVE6001 or pVE6002 are cultured at 28° C. or 37.5° C. After different culture times, samples are removed and cultured at 28° C. on selective and non-selective media. 100 colonies are subcultured from the non-selective medium on the selective medium (Em 5 µg/ml) in order to evaluate the proportion of cells containing a plasmid in the population. Extractions of total DNA are done on the cultures at 28° C. or 37.5° C., without selection, for 5 h 30 min.

FIG. 2: Hybrid plasmid of pGK12 and pVE6002. pVE6043 consists of the 994-bp Sac I-Tha I fragment of pGK12 linked to the 3384-bp Tha1-Sac1 [sic] fragment of pVE6002. pVE6044 contains the reciprocal pair, the 994-bp Sac I-Tha I fragment of pVE6002 linked to the 3384-bp Tha I-Sac I fragment of pGK12. The thin lines correspond to the pGK12 DNA; the thick dotted lines to the pVE6002 DNA.

FIG. 5: Comparison of proteins analogous to Rep of PE.194.

FIG. 7a: Diagram of an example of excision of the Ts replicon in two steps.

FIG. 7b: Diagram of excision of the replicon by means of plasmid duplications.

FIG. 9: Nucleotide sequence of pG+host4.

FIG. 10: Nucleotide sequence of pG+host5.

FIG. 11 : Nucleotide sequence of pG+host6.

DETAILED DESCRIPTION OF THE INVENTION

Figure 2:
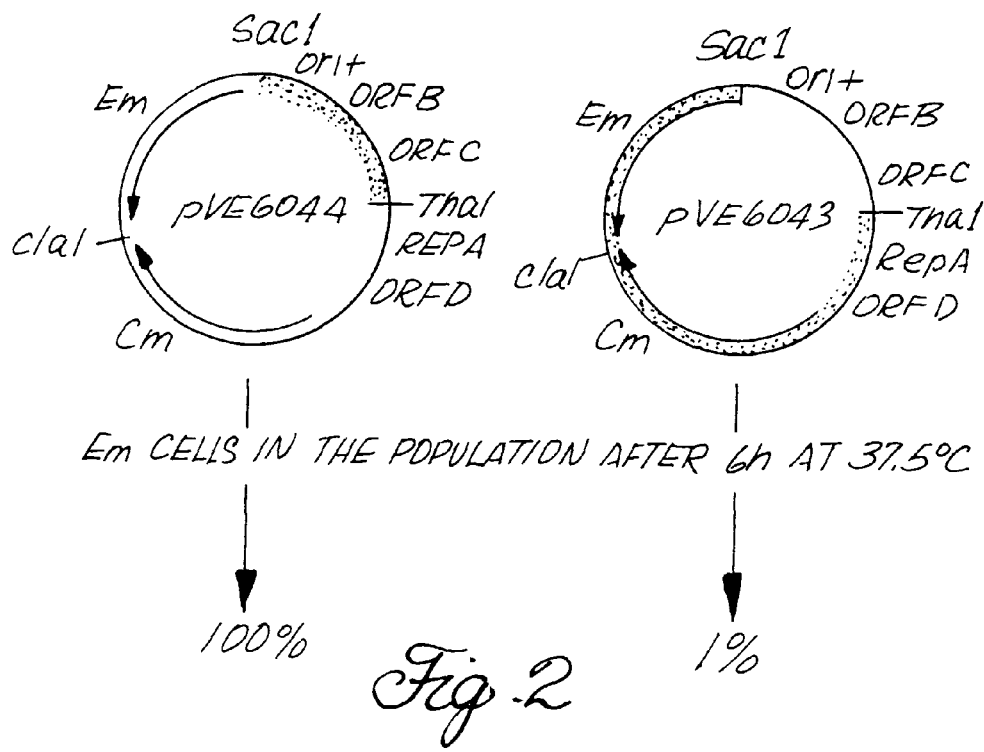

The examples which follow are designed to illustrate the invention without in any way limiting its scope.

EXAMPLE 1

Preparation and characterization of a temperature-sensitive vector plasmid

MATERIALS AND METHODS

The work was carried out at the Laboratoire de Genetique Microbienne, Institut de Biotechnologie [Microbial Genetics Laboratory, Biotechnology Institute], INRA, 78352 Jouy-en-Josas cedex France.

Bacterial strains, plasmids and culture conditions.

The plasmids and the bacterial strains used are shown in Table 1. The constructions of pVE6043 and pVE6044 are described in FIG. 2; plasmids pVE6004, pEV6006 and pVE6007 are presented in FIG. 4. pVE6004 (or pG$^+$host4) is constructed by insertion of a 445-bp PvuII DNA fragment into the blunt-ended 3340-bp ClaI-HpaII fragment of the original Ts isolate, lacking the Cm resistance gene. The 445-bp PvuII fragment contains a multicloning site, the T7 and T3 promoters and the sites for M13-20, T7, T3 and reverse primers which permit direct sequencing from the vector. This plasmid is temperature-sensitive in all the hosts tested including E. coli, and must be maintained at 28° C.

E. coli and Bacillus subtilis were cultured in LB medium. L. lactis subsp. lactis (L. lactis) is cultured on M17 medium in which lactose has been replaced by glucose. Chloramphenicol (Cm) was used at a concentration of 5 μg/ml for L. lactis and B. subtilis, respectively, and erythromycin (Em) at a concentration of 5 μg/ml and 0.5 μg/ml, respectively. Cm, azaerythromycin and erythromycin were used at respective final concentrations of 15 μg/ml, 100 μg/ml and 150 μg/ml for E. coli.

Molecular cloning, competence and transformation procedure.

Commercial enzymes were used as directed by the suppliers. Minilysates of whole cells and of plasmid DNA were prepared as described in the literature. The induction of competence and the transformation of E. coli and of B. subtilis were performed by standard procedures (Hanahan, 1985, or Niaudet et al., 1979). L. lactis strains were electrotransformed as described by Langella and Chopin, 1989a, the procedure being as modified by Holo and Nes, 1989.

TABLE 1

LIST OF STRAINS AND PLASMIDS

| Strain or plasmid | Genetic markers or description | Origin or reference |
|---|---|---|
| BACTERIAL STRAINS | | |
| L. lactis: IL1403 | Lacking plasmid, R$^-$ M$^-$, 2 prophages b1285 and b1286 | Chopin et al., 1984 |
| MG1363 | Lacking plasmid | Gasson, M. J. 1983 |
| B. subtilis: SB202 | trpC2, tyrA1, aroB2, hisH2, thyA | INRA laboratory |
| E. coli: DH5 | F$^-$endA1 recA1_ hsdR17 (r$_k^-$ m$_k^+$) supE44 thi1 gyrA96 relA1 | Hanahan, D. 1985 |
| PLASMIDS | | |
| pBluescript | Ap$^r$ M13-ori pBR322-ori | Strategene |
| pGK12 | Em$^r$ Cm$^r$ | Kok et al., 1984 |
| pVE6004 | 445-bp frgt of pBluescript and 3340-bp ClaI-HpaII frgt of pVE6002 Em$^r$ | Present invention |
| pVE6006 | 445-bp frgt of pBluescript inserted into the ClaI site of pVE6002 Em$^r$ Cm$^r$ | FIG. 4 |
| pVE6007 | ScaI [sic] deletion of 1175-bp from pVE6006 Cm$^r$ | Present invention |
| pVE6043 | SstI-ThaI frgt (ori+) of pGK12 ThaI-SstI frgt (ORF A) of pVE6002 Em$^r$ Cm$^r$ | Present invention |
| pVE6044 | SstI-ThaI frgt (ori+) of pVE6002 ThaI-SstI frgt (ORF A) of pGK12 Em$^r$ Cm$^r$ | FIG. 2 |

Mutagenesis of plasmids.

Hydroxylamine mutagenesis was performed on plasmid pGK12 DNA under the conditions described by Thomas, 1987. After 110 and 120 minutes of treatment at 70° C., the hydroxylamine is removed by isopropanol precipitation of the DNA.

DNA sequencing.

For sequencing of the DNA, the Tha1 [sic] (756 bp)-RsaI (1620 bp) fragment of pVE6002 was cloned into plasmid pbluescript. A series of overlapping clones is generated by the use of exonuclease III and mung bean nuclease (Strategene). The Tha1 [sic] (756 bp)-Nde I (1140 bp) fragment of the preparation of plasmid pGK12 used for the mutagenesis is also sequenced by the same procedure.

DNA sequencing is carried out by the dideoxy chain termination method on double-stranded DNA with the Taq Dye Primer Cycle Sequencing Kit (Applied Biosystem) using a Perkin Elmer PCR apparatus. The sequencing reactions are initiated with fluorescent oligonucleotides (Applied Biosystem) and are analyzed on an automatic sequencer (370 A DNA sequencer, Applied Biosystem). The sequences obtained were determined on both strands.

RESULTS

Isolation of the mutant.

The plasmid used in these experiments, pGK12, is a derivative of pWV01 containing two markers for resistance to antibiotics (KoK [sic] et al., 1984). 10 μg of plasmid DNA are mutagenized in vitro with hydroxylamine and introduced by electroporation into lactococcus strain IL 1403 after removal of the mutagenic agent. The efficacy of the mutagenesis is evaluated by the decrease in viability of the plasmid and by the appearance of mutants sensitive to erythromycin or to chloramphenicol. After 110 to 120 minutes of treatment, the viability of the plasmid falls to less than 0.1% and approximately 10% of the transformants contain plasmids sensitive to one of the antibiotics. These mutagenesis conditions are chosen in order to look for temperature-sensitive plasmids, identified by replication of the transformants obtained at 28° C. on a medium containing erythromycin with the transformants being incubated at 37.5° C. Two temperature-sensitive candidates, designated pVE6001 and pVE6002, are obtained by screening approximately 5000 clones. Their plasmid copy numbers are compared, and the loss at 37.5° C. is determined.

Characterization of the mutant: pVE6001 is a non-Ts mutant.

Plasmid pVE6001 is more unstable than pGK12 at 28° C., and this deficiency becomes more pronounced at 37.5° C. However, 7% of the bacteria still contain the plasmid after 8 hours of non-selective growth at 37.5° C., suggesting that a replication takes place under restrictive conditions (FIG. 1A, left).

Compared to pGK12, the copy number of pVE6001 is seen to be decreased at 28° C. and 37.5° C., with or without selection (FIG. 1A), which might explain its lower stability. It is possible that the loss of the plasmid at high temperatures is due to physiological changes in the host at higher temperatures, and not to the temperature sensitivity of the plasmid.

Characterization of the mutant: pVE6002 is a temperature-sensitive mutant above 35° C.

Measurements of the stability of the plasmid during growth without antibiotic reveal that pVE6002 is as stable as pGK12 at 28° C., but is lost drastically at 37.5° C. (FIG. 1B). The rapid loss of pVE6002 at 37.5° C. suggests that replication is blocked immediately after the change in temperature. After 8 hours of growth, only approximately 0.1% of erythromycin-resistant cells remain. The copy numbers of pGK12 and of pVE6002 are similar at 28° C., with and without selection; however, after 5 hours at 37.5° C., pVE6002 is undetectable, whereas the copy number of pGK12 is roughly the same (FIG. 1B). It may be concluded from these experiments that the mutation on pVE6002 genuinely constitutes a temperature-sensitive deficiency of replication.

The minimum temperature permitting the loss of pVE6002 was determined. The strain IL1403 containing pVE6002 was tested for plasmid loss during 8 hours of non-selective growth at 28° C., 30° C., 33° C., 35° C. and 37.5° C. (Table 2).

TABLE 2

Percentage of Em$^r$ cells in the population

| | Growth temperature | | | | |
|---|---|---|---|---|---|
| Time (Hours) | 28° C. | 30° C. | 33° C. | 35° C. | 37.5° C. |
| 0 | 100 | 100 | 100 | 100 | 100 |
| 2 | 100 | 100 | 99 | 97 | 98 |
| 4 | 100 | 100 | 48 | 47 | 38 |
| 6 | 100 | 100 | 9 | 3 | 4 |
| 8 | 100 | 99 | 5 | 1 | 1 |

An overnight culture of IL1403 carrying pVE6002 in M17 with Em is diluted in fresh selective medium and allowed to grow for 3 hours at 28° C. The culture is then diluted 10,000 times in a non-selective medium and incubated at different temperatures. At various time intervals, samples are taken and placed on M17 at 28° C. For each temperature and time point, the loss of the plasmid is evaluated by subculturing around a hundred colonies on dishes of selective medium (Em) at 28° C.

It was found that the plasmid loss is equivalent at 37.5° C. and 35° C. Partial loss of the plasmid is already observed at 33° C., whereas the plasmid was stable at 28° C. and 30° C. Thus, cells containing pVE6002 can lose this plasmid by raising the temperature to 35° C. or more.

pVE6002 was also introduced into another strain of Lactococcus, MG1363 (Gasson, 1983), which differs from IL1403 by comparison of the pulsed-field electrophoresis profiles. Sequence analysis indicates that MG1363 is probably a L. lactis subsp. cremoris strain (Godon et al., 1992). pVE6002 shows the same temperature sensitivity in this environment, demonstrating that the phenotype of the plasmid mutant is not linked to the strain.

Broad host range and Ts phenotype of pVE6002.

A Ts plasmid can be a cloning vehicle which is useful in other organisms. Thus, the temperature-sensitive behavior of pVE6002 was examined in B. subtilis and E. coli. These strains were chosen as representatives of the broad host range of the original replicon pWV01. The plasmid DNA was introduced into both species by transformation and selection at 28° C. In view of the fact that B. subtilis and E. coli have maximum growth temperatures higher than those of L. lactis subsp., the replication of pVE6002 was tested at 28° C., 37° C. and 42° C. The results show that pVE6002 is temperature-sensitive in both hosts. It is probable that pVE6002 retains its temperature sensitivity properties in the broad range of hosts in which it can be established.

Mapping of the Ts mutation.

The DNA sequence of pWV01 shows the presence of an origin-plus and of four ORFs. Leenhouts deduces from its similarity with better characterized plasmid DNAs that the ORF A codes for the replication protein (RepA) responsible for the cleavage of a DNA strand at the origin-plus. Further homologies suggest that ORF C might regulate the expression of RepA. Functions have not yet been clearly assigned to ORF B and ORF D, although it is known that the latter is not needed for replication.

In order to localize the mutation which confers temperature sensitivity on pVE6002, hybrid plasmids combining portions of the temperature-sensitive replicon and unmutated portions were constructed. pVE6043 consists of a fragment of pGK12 containing the origin-plus, ORF B and ORF C, and of a pVE6002 fragment (Ts) containing ORF A (RepA) lacking its promoter, ORF D and the markers for resistance to Em and Cm (the Sac I and Tha I restriction sites are used, FIG. 2). This hybrid is lost at 37.5° C., at the same rate as pVE6002, whereas the reciprocal hybrid (pVE6044) is maintained with the same stability as pGK12 (FIG. 2). Thus, the mutation conferring temperature sensitivity on pVE6002 is located in the DNA fragment coding for RepA, ORF D and the markers for antibiotics. In view of the fact that ORF D is not essential and that the markers for antibiotics are not candidates, it may be concluded that the temperature-sensitive function is the RepA protein.

Sequencing data.

Figure 3:
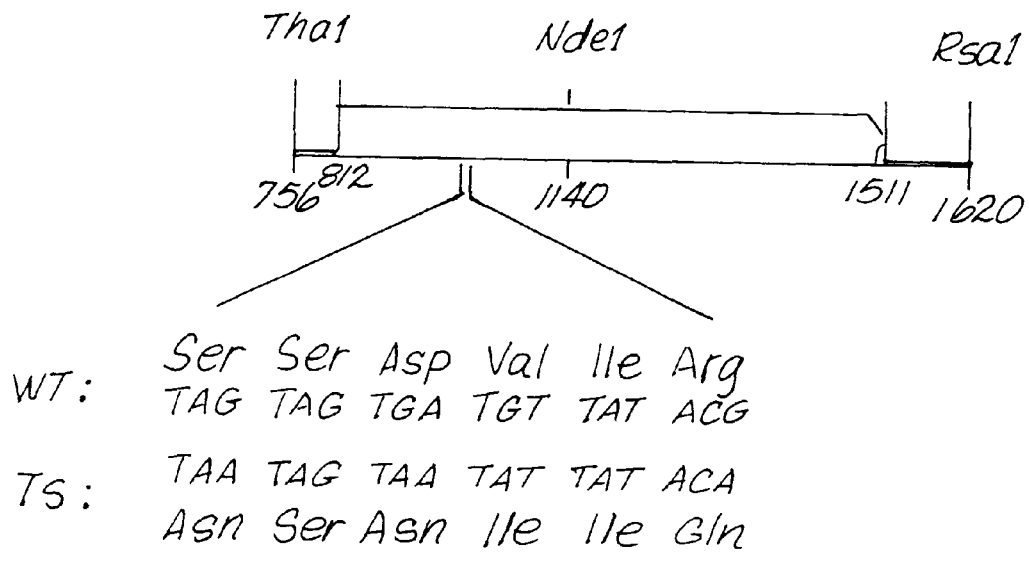
FIG. 3: Localization of the Ts mutation in the RepA gene of pVE6002. The Tha I-Rsa I fragment of pVE6002, containing the RepA gene, was sequenced on both strands. The sequence shows four mutations at positions 972, 977, 980 and 987, whereas the remainder of the sequence does not differ from the sequence published for the parent replicon pWV01.

In order to localize the Ts mutation, the 864-bp fragment coding for the RepA protein of pVE6002 was sequenced. Four mutations were identified, at positions 972, 977, 980 and 987 (FIG. 3). It was confirmed that the corresponding region of the parent plasmid pGK12 which was used for the mutagenesis is identical to the sequence published for pWV01 (Leenhouts et al., 1991). The four mutations are transitions of G to A, corresponding to the known mutagenic effect of hydroxylamine. Each change in base results in an alteration of an amino acid (FIG. 3), one of which, Val to Ile, is conservative. The contribution of one or more of these alterations may be involved in the Ts phenotype.

Derivatives of the Ts plasmid.

Figure 4:
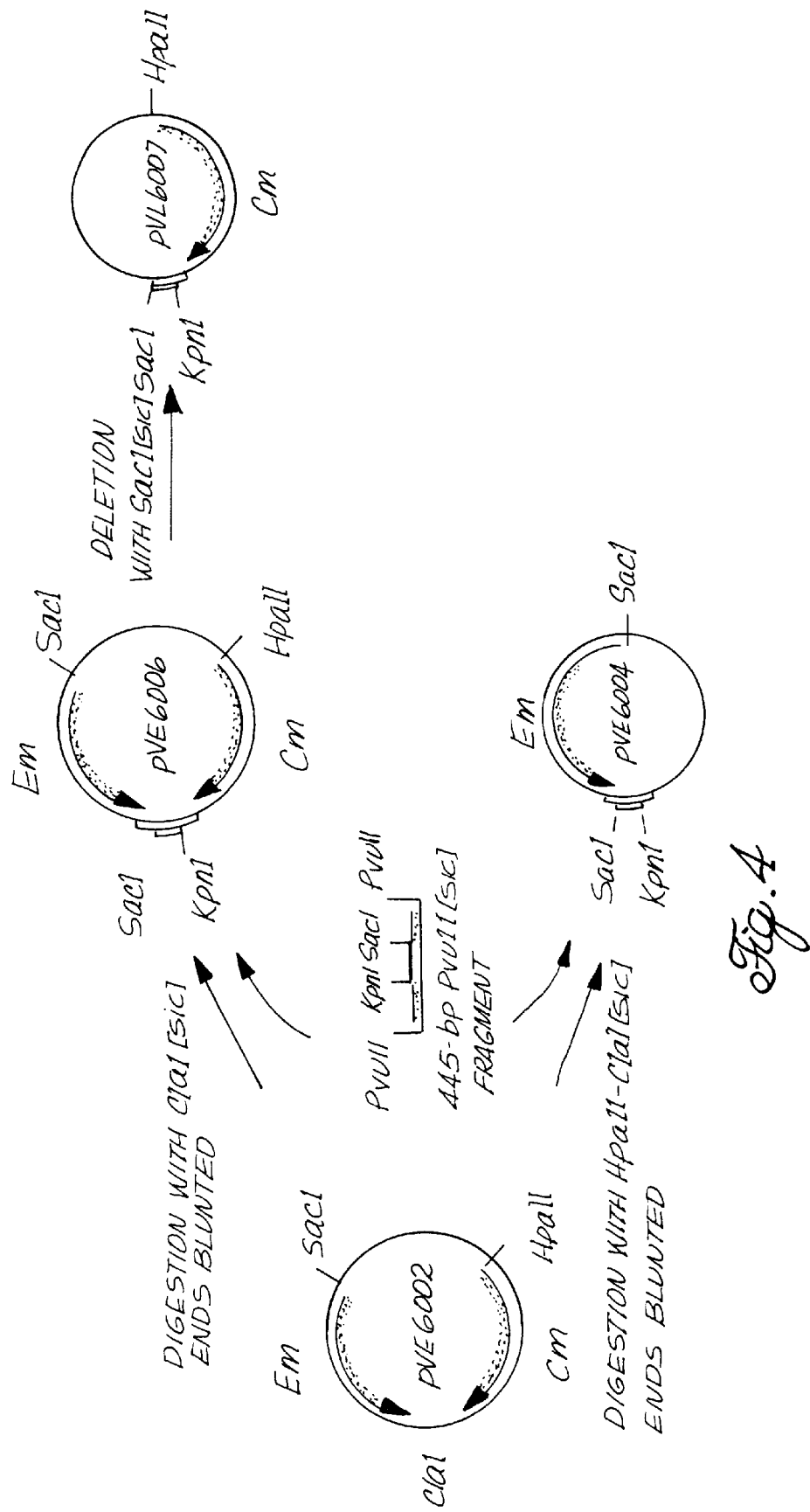
FIG. 4: Description of the temperature-sensitive derivatives. pVE6006 is constructed by insertion of the 445-bp PvuII fragment of pBluescript SK+ into the Cla I site of pVE6002. pVE6007 originates from a Sac I deletion from pVE6006, leading to loss of the gene for resistance to erythromycin. pVE6004 is constructed by insertion of the 445-bp PvuII fragment of pBluescript SK+ into the Cla I-Hpa II fragment of pVE6002 lacking the gene for resistance to chloramphenicol.
Figure 6:
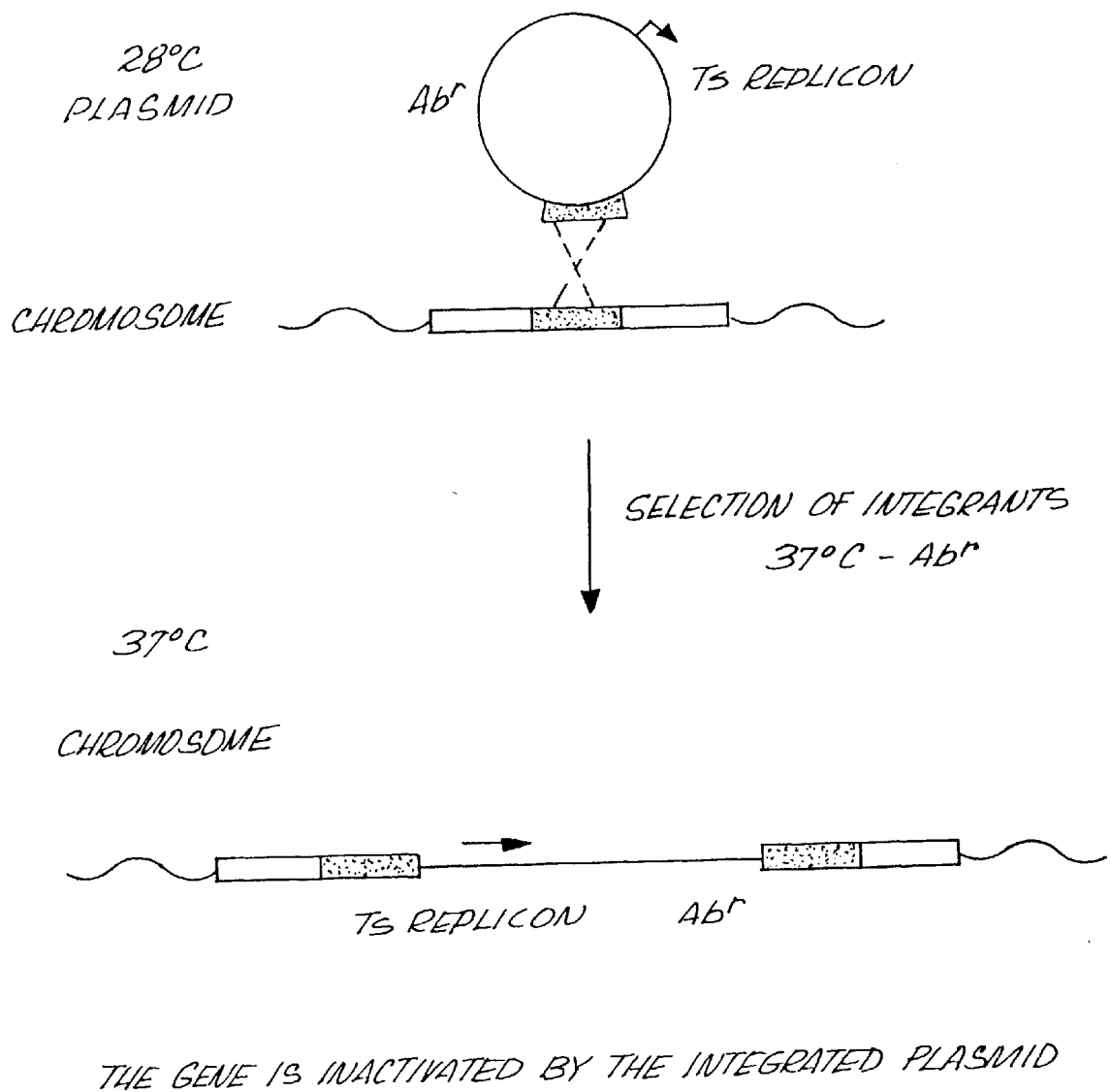
FIG. 6: Diagram of the method for the inactivation of a gene.

With the object of cloning, derivatives of the initial Ts plasmid pVE6002 were developed (FIG. 4). These derivatives are modified to contain either both antibiotic resistances (Em and Cm) or only one (Em or Cm), and they all have a multisite sequence derived from plasmid pBluescript SK+.

Excision of the replicon.

It was possible to obtain double reciprocal exchange events from a plasmid derived from pVE6002 carrying a region of homology with the bacterial chromosome interrupted by a gene for resistance to an antibiotic (Ab$^r$), as illustrated in FIG. 7a. After introduction of the plasmid into the bacterium at 28° C., a first step consists in selecting the integrants in the chromosome by culture at 37° C. on medium containing the antibiotic. The region of homology is duplicated following integration (FIG. 7a). In a second step, excision of the replicon is obtained by incubation at 28° C. in order to enable plasmid replication to resume and to stimulate a second recombination event. The excision events are selected by culture at 37° C.; the chromosomal gene is inactivated by the Ab$^r$ gene.

EXAMPLE 2

Integration of the temperature-sensitive plasmid in the chromosome of *L. lactis*.

The bacterial strains and the plasmids used in this study are presented in Table 3. The *Escherichia coli* strains are cultured in LB broth. *L. lactis* is cultured and plated out on an M17$^-$ glucose broth or on a minimum medium when it is tested for the ilv phenotype. Erythromycin (Em) is added at a concentration of 5 micrograms/ml for *L. lactis* subsp. *lactis* and 150 micrograms/ml for *E. coli*, and tetracycline is used at a concentration of 12.5 micrograms/ml for *L. lactis*. Electroporation of *L. lactis* subsp. *lactis* (Appl. Env. Microbiol. 55, 3119–3123, 1989) gives between 10$^5$ and 10$^6$ transformants per microgram of plasmid DNA for IL1403, and approximately 10$^2$ transformants per microgram of plasmid DNA with NCDO2118, the ilv$^+$ strain used for the gene replacement experiments. *E. coli* is transformed by the method described by Hanahan (1985, DNA cloning: A practical approach Vol 1: 109–135, IRL Press Ed Glover).

TABLE 3

| | GENETIC MARKERS OR DESCRIPTION | SOURCE |
|---|---|---|
| STRAIN | | |
| *L. lactis*: NCD02118 | natural usolate | * |
| *E. coli*: TG1 | supE hsdΔ5 thi Δ(lac-proAB)F[traD36pro-AB+lacI$^q$lacZΔM15] | Sambrook et al. |
| PLASMID | | |
| pg+host4 [sic] or pV6004 | temperature-sensitive derivative of pGK12, Em$^r$ | ** |
| pG+host5 [sic] | NsiI frag. of pG+host4 linked to the 1.46-Kb AvaI-AlwNI fragment of pBR322 Em$^r$ | ** |
| pVE7021 to pVE7034 | SmaI-HindIII restriction product of pG+host5 [sic] | ** |

TABLE 3-continued

| | GENETIC MARKERS OR DESCRIPTION | SOURCE |
|---|---|---|
| | linked to a random EcoRV-HindIII fragment of the IL1403 chromosome | |
| pIL515 | 3.9-Kb ilv EcoRI frag. of IL1403 in pBluescript, Amp$^r$ | ** |
| pVE7009 | 3.9-kB EcoRI frag. of pIL515 linked to pG+host5 [sic] cut with EcoRI | ** |
| pVE7009R | same construction as pVE7009, inserted in the opposite orientation | ** |
| pVE7015 | SphI-EcoRV deletion from pVE7009R leaving a 3362-bp ilv frag. | ** |
| pVE7014 | StyI-EcoRV deletion from pVE7009R leaving a 2904-bp ilv frag. | ** |
| pVE7010 | ClaI deletion from pVE7009R leaving a 2552-bp ilv. frag. | ** |
| pVE7016 | XcmI-EcoRV deletion from pVE7009R leaving a 1912-bp ilv frag. | ** |
| pVE7013 | AatII-EcoRV deletion from pVE7009R lreaving a 1206-bp ilv frag. | ** |
| pVE7011 | HindIII deletion from pVE7009R leaving a 497-bp ilv frag. | ** |
| pVE7012 | PstI deletion from pVE7009R leaving a 356-bp ilv frag. | ** |
| pVE7017 | PflMI-EcoRV deletion from pVE7009R leaving a 330-bp ilv frag. | ** |
| pIL500 | 18.5-Kb ilv XbaI frag. of NDCO2118 chromosome in pIL253 | Godon et al. |
| pIL1202 | XbaI frag. of pG+host4 [sic] containing the 1.1-Kb XbaI-BglII and 2.5-Kb EcoRI-XbaI ends of the 18.5-Kb frag. of pIL500 linked to the 4-Kb BamHI frag. of the Tet M gene | |
| pIL1261 | 2.3-Kb XbaI-EcoRI frag. of pIL500 interrupted by a Tet M gene, 4-Kb BamHI inserted at the BglII site and linked to pBluescript XbaI-EcoRI | |
| pIL1263 | pG+host4 [sic] XbaI-EcoRI linked to the 6.3-Kb XbaI-EcoRI frag. of pIL1261 | |

*National Collection of Dairy Organisms
**Present invention

Construction of plasmids for integration.

a) construction of the vector

Figure 8:
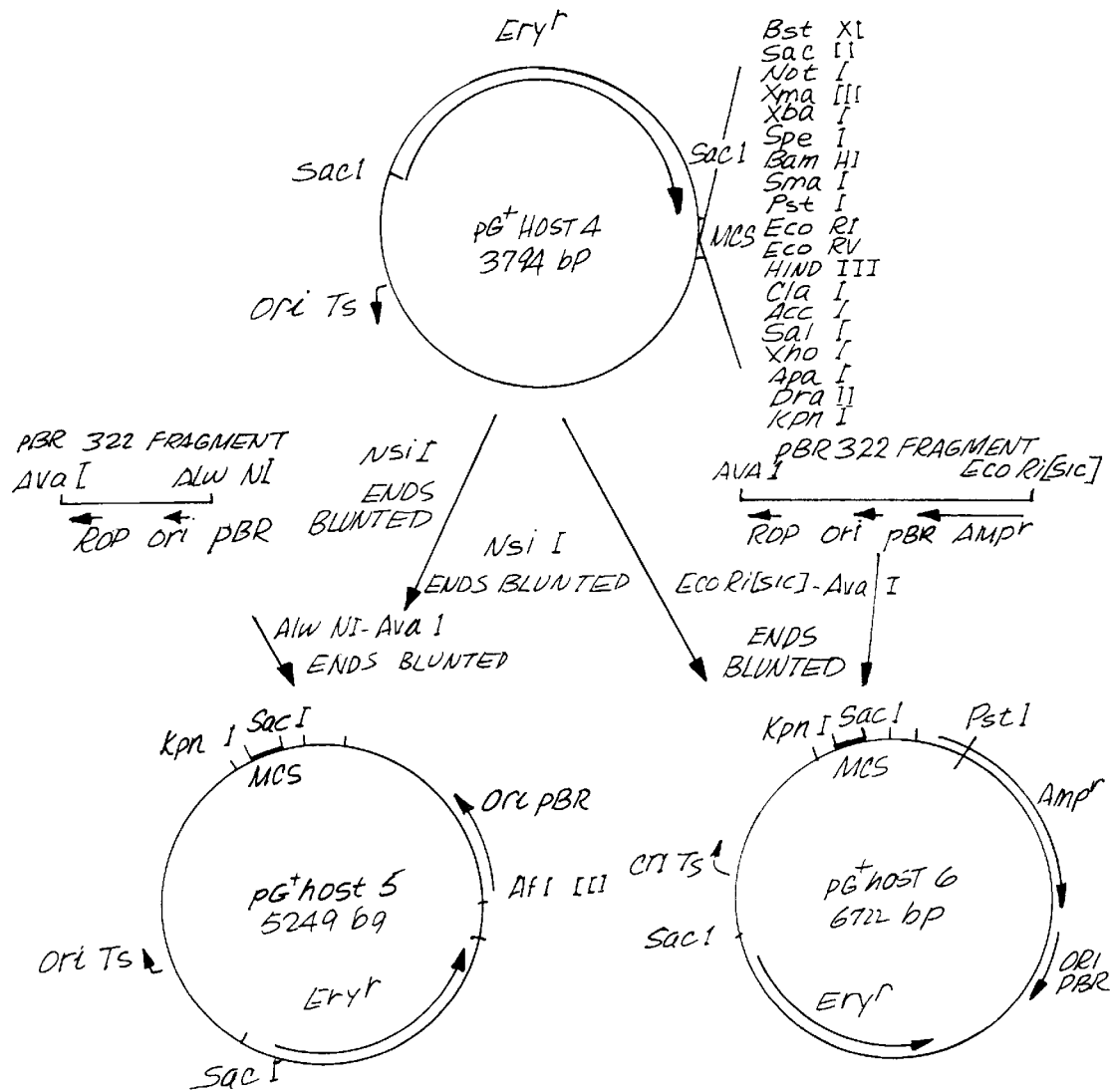
FIG. 8: Construction of plasmids pG+host5 and pG+host6 from plasmid pG+host4 (or pVE6004): plasmid pG+host5 is constructed by insertion of the Ava I-Alw N I fragment of pBR 322 (which contains the origin of replication of pBR 322) into pG+host4 linearized with Nsi I. pG+host6 is constructed by insertion of the Ava I-Eco R I fragment of pBR 322 (which contains the origin of replication of pBR 322 and the gene for resistance to ampicillin) into pG+host4 linearized with Nsi I.

Plasmid pG$^+$host4 (or pVE6004) is a Ts derivative of pWV01 prepared according to Example 1. To facilitate cloning in *E. coli*, the 1.4-Kb fragment containing the origin of pBR322 is inserted into pG$^+$host4. Plasmid pG$^+$host5 is constructed by insertion of the Ava I-Alw N I fragment of pBR 322 (which contains the origin of replication of pBR 322) into linearized pG$^+$host4 cut with Nsi I. Its structure is shown in FIG. 8. The plasmid obtained, referred to as pG$^+$host5 (Appligène, Illkirch, France) is used for all the clonings. The activity of the origin of pBR322 permits its maintenance at 37° C. in *E. coli*, and the Ts origin maintains pG$^+$host5 at 28° C. in Gram-positive bacteria.

b) cloning of random chromosomal fragments into pG$^+$host5.

Chromosomal DNA of the strain IL1403 is digested with EcoRV and HindIII. Chromosomal fragments between 0.9

Kb and 1.4 Kb in size are purified from agarose gels and linked with pG+host5 treated with SmaI-HindIII. The recombinant plasmids are established in E. coli, and then introduced into L. lactis by electroporation. The latter organism is used to verify the structures of the plasmids and the sizes of the inserts. The results are presented in Table 4 below. The restriction enzymes Hpa1 [sic] (single site in the vector portion) and HindIII (single site between the insert and the vector) are used to analyze the integrants.

TABLE 4

Ipc at different localizations on the L. lactis chromosome

| Size of the plasmid insert | | IPC |
|---|---|---|
| | (Kb) | mean ± SD |
| Group I: | | |
| pVE7025 | 1.29 | $3.0 \pm 0.3 \times 10^{-2}$ |
| pVE7034 | 1.05 | $3.8 \pm 0.5 \times 10^{-3}$ |
| pVE7021 | 1.29 | $3.4 \pm 2.6 \times 10^{-3}$ |
| pVE7024 | 0.96 | $2.5 \pm 1.3 \times 10^{-3}$ |
| pVE7030 | 1.42 | $2.3 \pm 0.8 \times 10^{-3}$ |
| pVE7028 | 1.46 | $7.2 \pm 0.7 \times 10^{-4}$ |
| pVE7023 | 1.29 | $6.6 \pm 3.9 \times 10^{-4}$ |
| pVE7022 | 1.08 | $5.7 \pm 0.3 \times 10^{-4}$ |
| pVE7027 | 1.05 | $5.2 \pm 1.3 \times 10^{-4}$ |
| pVE7026 | 0.96 | $4.0 \pm 0.5 \times 10^{-4}$ |
| Group II: | | |
| pVE7029 | 1.02 | $1.1 \pm 0.4 \times 10^{-5}$ |
| pVE7031 | 0.96 | $9.9 \pm 3.9 \times 10^{-6}$ |
| pVE7032 | 1.37 | $8.6 \pm 5.0 \times 10^{-7}$ |
| pVE7033 | 1.25 | $3.9 \pm 0.9 \times 10^{-7}$ | ipc: Frequency of integrations per cell c) cloning and deletion of an ilv operon fragment A 3949-bp EcoRI fragment of the ilv operon of IL1403 (J. Bacteriol 174, 6580–6589 (1992) [lacuna] is cloned in either orientation at the Eco RI site of pG+host5 (to give pVE7009 and pVE7009R).

Integration by single crossing-over (sco) in the L. lactis chromosome

Lactococcus strains containing the test plasmids are cultured overnight at 28° C. in the presence of erythromycin, then diluted 100 times in the same medium and cultured at 28° C. for 2 hours to 2½ hours (exponential phase). The cultures are placed at 37.5° C. for 3 hours in order to decrease the number of copies of plasmids per cell. The samples are then diluted and plated out at 37° C. on M17 Em medium in order to detect the integration events, and at 28° C. on non-selective medium to determine the number of viable cells. The frequency of integration per cell (ipc) is estimated as the ratio of $Em^r$ cells at 37° C. to the number of viable cells at 28° C. The integrants isolated at 37° C. are maintained in an M17 medium containing Em at 37.5° C. for subsequent use.

Integration by double crossing-over (dco) in the L. lactis chromosome

Plasmids pIL1263 and pIL1202 are composed of the Ts vector (pG+host4, $Em^r$) and, respectively, the 2.3-Kb or 3.6-Kb chromosomal regions interrupted by the Tet gene of Tn1545 (Nucl. Acids Res., 14, 7047–7058, 1986). A strain carrying pIL1202 or pIL1263 is cultured overnight at 37.5° C. in M17 with Tet or Em to obtain a population of integrants. The culture is then diluted to $\frac{1}{10^5}$ in M17 medium without antibiotic, and brought to 28° C. in order to stimulate recombination by plasmid replication. Culturing for 12 hours or more at 28° C. gives maximum gene replacement frequencies. An overnight culture at 28° C. is plated out at different cell concentrations at 37° C. with or without selection by Tet. Colonies in which gene replacement has taken place have a $Tet^r$ and Em-sensitive ($Em^s$) phenotype. Chromosomal DNA is prepared according to known methods (Gruss et al., 1988).

The purified DNA is treated with restriction enzymes, separated by agarose gel electrophoresis and analyzed by Southern hybridization with DNA probes to detect homologous recombinations (Sambrook et al., 1989).

Results

1) Integration by single crossing-over

The cloning of chromosomal fragments of L. lactis into pG+host5 in E. coli enables 14 different plasmids each containing a different chromosomal insertion, from 0.9 Kb to 1.4 Kb, to be isolated. These plasmids established in IL1403 at 28° C. are used to measure the frequencies of integration in the L. lactis chromosome. The frequency of integration per cell is between $10^{-2}$ and $10^{-7}$. The ipc of a pG+host5 vector without chromosomal insert is between $10^{-6}$ and $10^{-7}$. Plasmids carrying the chromosomal inserts may be classified in two groups in accordance with their frequency of integration. In group I, the ipc varies between $3 \times 10^{-2}$ and $4 \times 10^{-4}$. These variations must be due to the localization or the nature of the insert rather than to its size. In group II, the ipc of the plasmid is between $10^{-5}$ and $3 \times 10^{-7}$. This is probably due to the interruption of an essential chromosomal gene, which enables only non-homologous integrations to be observed. Only two of these plasmids (pVE7028 and pVE7034) produce high molecular weight (HMW) molecules. Analysis of the chromosomal DNA obtained from the integrant strains maintained at 37° C., by enzymatic restriction and Southern hybridization using plasmid pG+host5 as probe, indicates a single and multi-tandem integration in the case of eight plasmids and an integration by multiple copies in the case of two plasmids. Digestion of the DNA of the integrants with HindIII confirms that the integration takes place by single crossing-over. Each plasmid contains only one HindIII site at the vector-insert junction, and digestion should liberate a single band of plasmid-sized DNA. Southern hybridization of the undigested total DNA does not reveal a free plasmid in any of the group I plasmids, indicating that the copy of the plasmid is integrated. A similar analysis of plasmids pVE7028 and pVE7034 confirms that these plasmids are also integrated by single crossing-over. The use of HpaI, which recognizes a single site within the vector, enables it to be determined that each plasmid is integrated at a different position.

The four group II plasmids (low frequency of integration) appear to be integrated at random, since HindIII digestion does not liberate a monomeric band of plasmid, and HpaI digestion of three integrants of the same plasmid does not give the same profile on gel. The restriction map of the L. lactis chromosome developed for SmaI and ApaI enables the integration sites of the plasmids by single crossing-over to be localized on the chromosome map. Each integrant is present on a different segment. These results collectively indicate that the chromosomal insertions are positioned randomly on the chromosome, thus ruling out any bias in the procedure.

The frequency of integration depends on the length of homology.

A 3.9-Kb segment of the ilv operon of IL1493 which is sequenced is cloned into pG+host5, and a set of deletions from the fragment is generated on the same vector. Whereas plasmids carrying the total insert of 3.9 Kb in one of the two orientations (pVE7009 and pVE7009R) possess some degree of structural instability in *L. lactis,* the eight deletion derivatives of pVE7009R are stable. These clones are used to study the relationship between the length of homology and the frequency of integration. A logarithmic relationship exists between the frequency of integration and the length of homology for lengths between 0.35 and 2.5 Kb. For fragments over 2.5 Kb, the frequencies of recombination appear to reach a plateau, since the ipc values of homologous segments of 2.5, 3.3 and 3.9 Kb are not significantly different. Factors other than length are also seen to be important. Analysis with restriction enzymes which recognize a single site, either in the vector or in the insert or in the vector-insert junction, confirms that the integration takes place by homologous recombination by single crossing-over. For each plasmid used, multicopy integrations of the plasmid take place. These results show that pG+host provides an effective means of integration by single crossing-over if it carries homologous segments as small as 330 base pairs.

2) Integration by double crossing-over

In the single crossing-over (sco) system described above, the integrated plasmid is flanked by repeat sequences. Thus, when the integrant strains generated at 37° C. are placed at 28° C., replication of the plasmid strongly stimulates a second recombination event. The consequence of this event is a high frequency of excision of the replicon, leading either to the parent structure or to the dco (double crossing-over) chromosomal structure.

A weakly transformable strain of *L. lactis,* NCDO2118, which is prototrophic for the branched amino acids (Ilv, Leu, Val) and in which no genetic modification could be carried out hitherto, is used. Two derivatives of pG+host4 which carry either an adjoining or a non-adjoining chromosomal segment are used. pIL1263 contains a 2.3-Kb chromosomal fragment upstream of the ilv operon, interrupted by a 4-Kb DNA segment containing a marker for resistance to tetracycline (Tet$^r$). Substitution of the gene should lead to insertion of the Tet$^r$ marker into the chromosome and leave the ilv$^+$ operon intact. Plasmid pIL1202 contains non-adjoining 1.1-Kb and 2.5-Kb segments, corresponding to the ends of an 18.5-Kb region, including the ilv operon, joined via the 4-Kb Tet$^r$ marker. Replacement of the gene should lead to a deletion from the chromosome of 14.9 Kb including the ilv operon and giving an ilv$^-$ phenotype.

Selection of the replacement gene:

A strain containing either pIL1202 or pIL1263 is cultured under conditions described above, using Tet as selectable marker. In independent experiments with pIL1263, 69% and 98% of Tet$^r$ colonies were Em$^s$; with pIL1202, 50% and 91% of Tet$^r$ colonies are Em$^s$. In control cultures maintained at 37° C. for the same period, all the Tet$^r$ colonies are also Em$^r$. This result indicates that replication in rc plasmids (displaying circular replication) stimulates excision from the chromosome. Five Em$^s$ colonies obtained by integration of pIL1202 are cultured on minimum medium lacking branched amino acids and are ilv$^-$, thereby confirming that recombination has taken place. The structure of the corresponding chromosomal region of five Tet$^r$ Em$^s$ isolates is studied by Southern hybridization, which confirms the replacement of the gene in all the cases.

No selection:

An identical protocol was used without selection by Tet, so as to deal with the case where the chromosomal fragment carried by the plasmid does not have a selectable marker. In three experiments using pIL1263 (gene insertion), 10% to 40% of the colonies obtained at 37° C. without selection are Tet$^r$ Em$^s$, indicating that a gene replacement event has taken place. For pIL1202 (chromosome deletion), 1% to 7% of colonies are Tet$^r$ Em$^s$, indicating a replacement of the gene; of the four Tet$^r$ Em$^s$ colonies tested, all are ilv$^-$. Analysis of the chromosomal structure of the four dco integrants of each type confirms that replacement takes place without selection of a new inserted fragment. These results demonstrate the feasibility of gene replacement without leaving an antibiotic marker in the chromosome. This protocol is hence suited to chromosomal modification without the use of selectable markers. Use of pG+host in other Gram-positive bacteria The efficiency of intermolecular recombination in twelve different localizations of the *B. subtilis* chromosome was determined by transforming competent cells with a non-replicative plasmid (J. Bacteriol. 174, 5593–5587, 1992). In these experiments, the homologous segment is invariant (insertion of a fragment of pBR322). The efficiencies vary approximately threefold in accordance with the position of integration. Using the sco pG+host system instead of the non-replicative vector, experiments of identical recombination may be performed on the two *B. subtilis* strains with differences of an order of three in the frequencies of integration. pG+host5 carrying the 1.4-Kb fragment of pBR322 is introduced into the *B. subtilis* strains of interest. Using the sco procedure described above, the frequency of integration varies between $1.8 \pm 0.6 \times 10^{-3}$ and $6.1 \pm 0.9 \times 10^{-4}$. The same threefold variations are observed between the two different localizations as those obtained with the non-replicative system. This result demonstrates the efficiency of the system.

EXAMPLE 3

Genetic modification of non-transformable organisms

Organisms of industrial importance such as some lactobacilli are not at present transformable; it is, however, possible to introduce plasmids into them by conjugation. The mobilization locus oriT of plasmid pIP501 has been characterized. pIP501 is autotransferrable into some of these lactobacilli.

This oriT fragment was cloned into the Ts plasmid (plasmid Ts:oriT); its capacity to be mobilized in the presence of a helper plasmid (derived from pIP501), which provides the proteins for transfer in trans, was tested. Several intra- or inter-species crosses were carried out successfully (Table 5); with exconjugants which contain only plasmid Ts:oriT, the future method of integration by recombination is applicable. It is hence possible to introduce genetic information into the chromosome of *Lactobacillus bulgaricus,* a non-transformable species used increasingly by the dairy industry.

The objective of the method of integration by recombination is modification of the genetic characters of bacterial strains; this assumes that the properties to be modified are characterized at molecular level. The development of a functional transposition system (combination of the Ts plasmid of a transposon) would represent a considerable contribution as a genetic tool for the analysis of *L. lactis.*

TABLE 5

FREQUENCY OF CONJUGATION WITH PLASMID TS:oriT

| Donor<br>Recipient | L. lactis IL1403/pHelper/pTs:oriT |
|---|---|
| L. lactis IL1403 str$^r$ | $5 \times 10^{-3}$ exc/don* |
| E. faecalis IL1855 str$^r$ | $10^{-5}$ exc/don |
| L. bulgaricus IL1687 str$^r$ | $3 \times 10^{-5}$ exc/don |
| S. sanguis IL1474 str$^r$ | $3 \times 10^{-7}$ exc/don |

*exc/don: Number of exconjugants containing Ts:orit per donor cell

EXAMPLE 4

Use of a temperature-sensitive plasmid as vector for a transposon

A transposition cassette TN10 cloned into a derivative of pVE6004 is used for a transposition test. Approximately 1% of the cells are Em$^r$ at 37° C., indicating that the transposon or the plasmid is integrated in the chromosome. Non-specific integration of the plasmid without the transposition cassette takes place at frequencies of less than $10^{-7}$. Transposition is estimated by analysis of the DNA digested with HindIII from eight colonies. HindIII has two restriction sites in the plasmid but none in the transposable unit. The chromosomal DNA is extracted from eight Em$^r$ thermoresistant clones and digested with HindIII; the treated DNA is then separated by agarose gel electrophoresis and hybridized with a DNA fragment containing the Em$^r$ transposon as probe. Under these conditions, integration of the whole vector (that is to say without transposition) would lead to a hybridization band of 1.3 Kb, which is not observed here. Each chromosomal sample gives a single profile when the DNA fragment containing the transposon is used as probe. None of the hybridized bands has a size of 1.3 Kb, which would be expected if the whole plasmid were integrated in a site of the vector. In addition, hybridization is not observed when the Ts vector plasmid is used as probe. These results indicate that transposition takes place at different sites, and that the plasmid DNA does not integrate in the chromosome with the transposon. The temperature-sensitive plasmid may hence be used as a delivery vector.

LEGEND TO THE FIGURES

FIGURE 4:

Single sites:
AccI    KpnI
BamHI   NotI
BstXI   PstI
DraII   SalI
EagI    SacII
EcoRI   SmaI
EcoRV   SpeI
HindIII XbaI
        XhoI

FIGURE 6:

symbols:

  Active chromosomal gene

LEGEND TO THE FIGURES

 Region of homology between the plasmid and the chromosome

Ab$^r$      Resistance to an antibiotic

·     ·     Recombination event

FIGURE 7A:

symbols

 Active chromosomal gene

 Regions of homology between the plasmid and the chromosome

Tet$^r$    Resistance to tetracycline (Other markers may be used)

Em$^r$    Resistance to erythromycin

·.·  Recombination event

FIGURE 7B:

symbols:

 Active chromosomal gene

 Region of homology between the plasmid and the chromosome

 Plasmid duplication

Ab$^r$      Resistance to an antiniotic

·     ·     Recombination event

REFERENCES

Chopin, A., M C. Chopin, A. Moillo-Batt, and P. Langella. 1984. Plasmid II: 260–263.

Gasson, M. J. 1983, J. Bacteriol. 154: 1–9.

Godon, J.-J., C., Delorme, P., Renault and S. D. Ehrlich. 1992. Appl. Env. Microbiol. submitted.

Godon, J J., M C. Chopin and S. D. Ehrlich. 1992. J. Bacteriol. 174: 6580–6589.

Grüss, A., and S. D. Ehrlich. 1988. J. Bacteriol, 170: 1183–1190

Hanahan, D. 1985. In DNA cloning: A practical approach Vol. 1: 109–135. IRL Press Ed Glover.

Holo, H., and Nes, I, F. 1989. Appl. Env. Microbiol. 55: 3119–3123.

Kok. J., J. M. B. van der Vossen and G. Venema. 1984. Appl. Env. Microbiol. 48: 726–731.

Langella, P., and Chopin, A. 1989. FEMS Microbiol. Lett. 89: 301–306.

Leenhouts, K., J., B., Tolner, S., Bron, J., Kok, G., Venema and J., F. M. L. Seegers. 1991. Plasmid. 26: 55–66.

Niaudet, B; Ehrlich, S, D. 1979. Plasmid 2: 48–58.

Petit, M A., Mesas, M., J., Noirot, P., and Ehrlich, S., D. 1992. Inducible Amplification in the Bacterial Chromosome. submitted.

Sambrook J., F Fritsh, and T., E. Maniatis. 1989. Molecular cloning: a laboratory manual. Cold Spring Harbor Laboratory, Cold Spring Harbor, N.Y.

Thomas C. M. 1987. In Plasmids. A practical approach, IRL Press EDS Hardy.

We claim:

1. A bacterial vector plasmid containing an origin of replication which is effective in Gram-positive bacteria other than Streptomyces, wherein the plasmid contains at least:
   a marker gene which is expressed in a bacterial host strain,
   an effective replication system which is temperature-sensitive at and above a temperature compatible with the viability of the host strain, and wherein replication is inhibited at a temperature of below or equal to approximately 37° C.

2. The vector plasmid according to claim 1 further comprising a replication system which is effective in bacteria chosen from the group consisting of Bacillus, Enteroccocus, Lactobacillus, Lactococcus, Streptococcus, Listeria, Pediococcus, Staphylococcus, Clostridia, Leuconostoc, and E. coli.

3. The vector plasmid according to claim 1 further comprising at least one sequence, so as to permit recombination.

4. The vector plasmid according to claim 3, wherein the marker gene is located so as to be integrated in the chromosomal DNA sequence during recombination.

5. The vector plasmid according to claim 1 wherein the marker gene provides for resistance to a chemical compound or is a gene permitting complementation of an auxotrophy.

6. The vector plasmid according to claim 1 wherein that the temperature-sensitive replication system is inhibited above approximately 35° C.

7. The vector plasmid according to claim 1 wherein the plasmid contains a mobilization locus permitting conjugation.

8. The vector plasmid according to claim 7 wherein the mobilization locus is an ori T locus of a plasmid of a Gram-positive bacterium.

9. The vector plasmid according to claim 7 further comprising a replicon which is active in E. coli, making the plasmid a Gram-negative, Gram-positive shuttle plasmid.

10. The vector plasmid according to claim 1 comprising two identical repeat sequences flanking a sequence of the plasmid.

11. The vector plasmid according to claim 1 wherein the replication system is carried by the larger Cla I fragment of plasmid pWV01, possessing at least one mutation in the Tha I-Rsa I region.

12. The vector plasmid according to claim 11, comprising at least one mutation in the region corresponding to Rep A of plasmid pWVO 1.

13. The vector plasmid according to claim 11 comprising at least one mutation in at least one of positions 972, 977, 980 or 987 of pWVO1.

14. The vector plasmid according to claim 11 wherein the replication system codes for a protein possessing the mutations shown in FIG. 3.

15. The vector plasmid according to claim 11 wherein it is replicative at 28° C. and non-replicative at a temperature above approximately 35° C.

16. The vector plasmid according to claim 1 comprising one of the sequences shown in FIGS. 9, 10 or 11, or a sequence possessing at least 80% homology with these sequences.

17. The vector plasmid according to claim 1 comprising a transposon.

18. The vector plasmid according to claim 1 further comprising a gene coding for a protein of interest, under control of elements needed for its expression.

19. A bacterium, comprising a plasmid according to claim 1 in free form or integrated in its chromosome.

* * * * *